United States Patent
Han et al.

(10) Patent No.: US 9,687,377 B2
(45) Date of Patent: Jun. 27, 2017

(54) TERRAIN ADAPTIVE POWERED JOINT ORTHOSIS

(75) Inventors: Zhixiu Han, Acton, MA (US);
Christopher Williams, Pittsburgh, PA (US); Jeff A. Weber, San Francisco, CA (US); Christopher E. Barnhart, Carlisle, MA (US); Hugh M. Herr, Somerville, MA (US); Richard J. Casler, Jr., Lowell, MA (US)

(73) Assignee: BIONX MEDICAL TECHNOLOGIES, INC., Bedford, MA (US)

( * ) Notice: Subject to any disclaimer, the term of this patent is extended or adjusted under 35 U.S.C. 154(b) by 845 days.

(21) Appl. No.: 13/356,230

(22) Filed: Jan. 23, 2012

(65) Prior Publication Data
US 2012/0259431 A1    Oct. 11, 2012

Related U.S. Application Data

(60) Provisional application No. 61/435,045, filed on Jan. 21, 2011.

(51) Int. Cl.
| A61H 3/00 | (2006.01) |
| A61F 5/01 | (2006.01) |
| A61H 1/02 | (2006.01) |

(52) U.S. Cl.
CPC .......... *A61F 5/0125* (2013.01); *A61H 1/024* (2013.01); *A61H 3/00* (2013.01);
(Continued)

(58) Field of Classification Search
CPC . A61H 1/00; A61H 1/001; A61H 1/02; A61H 1/0237; A61H 1/024; A61H 1/0255;
(Continued)

(56) References Cited

U.S. PATENT DOCUMENTS

| 2,489,291 A | 11/1949 | Henschke at al. |
| 2,529,968 A | 11/1950 | Sartin |
| (Continued) | | |

FOREIGN PATENT DOCUMENTS

| EP | 1393866 | 3/2004 |
| WO | WO-03068453 | 8/2003 |
| (Continued) | | |

OTHER PUBLICATIONS

Abbas J. and Chizeck H., "Neural Network Control of Functional Neuromuscular Stimulation Systems: Computer Simulation Studies," IEEE Transactions on Biomedical Engineering, vol. 42, No. 1, Nov. 1995, pp. 1117-1127.

(Continued)

*Primary Examiner* — Justine Yu
*Assistant Examiner* — Tu Vo

(57) ABSTRACT

A powered device augments a joint function of a human during a gait cycle using a powered actuator that supplies an augmentation torque, an impedance, or both to a joint. A controller estimates terrain slope and modulates the augmentation torque and the impedance according to a phase of the gait cycle and the estimated terrain slope to provide at least a biomimetic response. The controller may also modulate a joint equilibrium. Accordingly, the device is capable of normalizing or augmenting human biomechanical function, responsive to a wearer's activity, regardless of speed and terrain, and can be used, for example, as a knee orthosis, prosthesis, or exoskeleton.

29 Claims, 18 Drawing Sheets

(52) U.S. Cl.
CPC .. *A61H 2003/001* (2013.01); *A61H 2201/165* (2013.01); *A61H 2201/1642* (2013.01); *A61H 2201/5007* (2013.01); *A61H 2201/5064* (2013.01); *A61H 2201/5084* (2013.01); *A61H 2201/5097* (2013.01); *A61H 2205/10* (2013.01); *A61H 2205/102* (2013.01)

(58) Field of Classification Search
CPC ............... A61H 1/0262; A61H 1/0259; A61H 2201/018; A61H 2201/12; A61H 2201/1207; A61H 2205/10; A61H 2205/106; A61H 2205/108; A61H 2205/102; A61H 3/00; A61H 2201/5007; A61H 2201/5097; A61H 2201/5064; A61H 2201/1642; A61H 2201/5084; A61H 2003/001; A61H 2201/165; A61F 5/01231; A61F 5/0193; A61F 5/0104; A61F 5/0123; A61F 5/0111; A61F 5/0113; A61F 5/0125
USPC ........... 601/5, 23, 33, 34, 35; 602/16, 23–29
See application file for complete search history.

(56) References Cited

U.S. PATENT DOCUMENTS

| | | |
|---|---|---|
| 3,098,645 A | 7/1963 | Owens |
| 3,207,497 A | 9/1965 | Schoonover |
| 3,844,279 A | 10/1974 | Konvalin |
| 4,442,390 A | 4/1984 | Davis |
| 4,463,291 A | 7/1984 | Usry |
| 4,518,307 A | 5/1985 | Bloch |
| 4,532,462 A | 7/1985 | Washbourn et al. |
| 4,546,295 A | 10/1985 | Wickham et al. |
| 4,546,296 A | 10/1985 | Washbourn et al. |
| 4,546,297 A | 10/1985 | Washbourn et al. |
| 4,546,298 A | 10/1985 | Wickham et al. |
| 4,569,352 A | 2/1986 | Petrofsky et al. |
| 4,600,357 A | 7/1986 | Coules |
| 4,657,470 A | 4/1987 | Clarke et al. |
| 4,843,921 A | 7/1989 | Kremer |
| 4,865,376 A | 9/1989 | Leaver et al. |
| 4,872,803 A | 10/1989 | Asakawa |
| 4,909,535 A | 3/1990 | Clark et al. |
| 4,921,293 A | 5/1990 | Ruoff et al. |
| 4,921,393 A | 5/1990 | Andeen et al. |
| 4,923,474 A | 5/1990 | Klasson et al. |
| 4,923,475 A | 5/1990 | Gosthnian et al. |
| 4,964,402 A | 10/1990 | Grim et al. |
| 4,989,161 A | 1/1991 | Oaki |
| 5,012,591 A | 5/1991 | Asakawa |
| 5,049,797 A | 9/1991 | Phillips |
| 5,062,673 A | 11/1991 | Mimura |
| 5,088,478 A | 2/1992 | Grim |
| 5,092,902 A | 3/1992 | Adams et al. |
| 5,112,296 A | 5/1992 | Beard et al. |
| 5,174,168 A | 12/1992 | Takagi et al. |
| 5,181,933 A | 1/1993 | Phillips |
| 5,252,102 A | 10/1993 | Singer et al. |
| 5,294,873 A | 3/1994 | Seraji |
| 5,311,109 A * | 5/1994 | Ozawa ..................... 318/568.11 |
| RE34,661 E | 7/1994 | Grim |
| 5,327,790 A | 7/1994 | Levin et al. |
| 5,367,790 A | 11/1994 | Gamow et al. |
| 5,383,939 A | 1/1995 | James |
| 5,405,409 A | 4/1995 | Knoth |
| 5,442,270 A | 8/1995 | Tetsuaki |
| 5,443,521 A | 8/1995 | Knoth et al. |
| 5,456,341 A | 10/1995 | Garnjost et al. |
| 5,458,143 A | 10/1995 | Herr |
| 5,476,441 A | 12/1995 | Durfee et al. |
| 5,502,363 A | 3/1996 | Tasch et al. |
| 5,514,185 A | 5/1996 | Phillips |
| 5,556,422 A | 9/1996 | Powell, III et al. |
| 5,571,205 A | 11/1996 | James |
| 5,643,332 A | 7/1997 | Stein |
| 5,650,704 A | 7/1997 | Pratt et al. |
| 5,662,693 A | 9/1997 | Johnson et al. |
| 5,701,686 A | 12/1997 | Herr et al. |
| 5,718,925 A | 2/1998 | Kristinsson et al. |
| 5,748,845 A | 5/1998 | Labun et al. |
| 5,776,205 A | 7/1998 | Phillips |
| 5,885,809 A | 3/1999 | Effenberger et al. |
| 5,888,212 A | 3/1999 | Petrofsky et al. |
| 5,898,948 A | 5/1999 | Kelly et al. |
| 5,910,720 A | 6/1999 | Williamson et al. |
| 5,932,230 A | 8/1999 | DeGrate |
| 5,971,729 A | 10/1999 | Kristinsson et al. |
| 5,972,036 A | 10/1999 | Kristinsson et al. |
| 5,980,435 A | 11/1999 | Joutras et al. |
| 6,029,374 A | 2/2000 | Herr et al. |
| 6,056,712 A | 5/2000 | Grim |
| 6,067,892 A | 5/2000 | Erickson |
| 6,071,313 A | 6/2000 | Phillips |
| 6,136,039 A | 10/2000 | Kristinsson et al. |
| 6,144,385 A | 11/2000 | Girard |
| 6,202,806 B1 | 3/2001 | Sandrin et al. |
| 6,223,648 B1 | 5/2001 | Erickson |
| 6,240,797 B1 | 6/2001 | Morishima et al. |
| 6,267,742 B1 | 7/2001 | Krivosha et al. |
| 6,416,703 B1 | 7/2002 | Kristinsson et al. |
| 6,443,993 B1 | 9/2002 | Koniuk |
| 6,456,884 B1 | 9/2002 | Kenney |
| 6,478,826 B1 | 11/2002 | Phillips et al. |
| 6,485,776 B2 | 11/2002 | Janusson et al. |
| 6,507,757 B1 | 1/2003 | Swain et al. |
| 6,511,512 B2 | 1/2003 | Phillips et al. |
| 6,517,503 B1 | 2/2003 | Naft et al. |
| 6,589,289 B2 | 7/2003 | Ingimarsson |
| 6,592,539 B1 | 7/2003 | Einarsson et al. |
| 6,610,101 B2 | 8/2003 | Herr et al. |
| 6,626,952 B2 | 9/2003 | Janusson et al. |
| 6,666,796 B1 | 12/2003 | MacCready, Jr. |
| 6,706,364 B2 | 3/2004 | Janusson et al. |
| 6,752,774 B2 | 6/2004 | Townsend et al. |
| 6,764,520 B2 | 7/2004 | Deffenbaugh et al. |
| 6,811,571 B1 | 11/2004 | Phillips |
| D503,480 S | 3/2005 | Ingimundarson et al. |
| D503,802 S | 4/2005 | Bjarnason |
| 6,887,279 B2 | 5/2005 | Phillips et al. |
| 6,923,834 B2 | 8/2005 | Karason |
| 6,936,073 B2 | 8/2005 | Karason |
| 6,945,947 B2 | 9/2005 | Ingimundarson et al. |
| 6,966,882 B2 | 11/2005 | Horst |
| 6,969,408 B2 | 11/2005 | Lecomte et al. |
| 6,992,455 B2 | 1/2006 | Kato et al. |
| 7,001,563 B2 | 2/2006 | Janusson et al. |
| 7,025,793 B2 | 4/2006 | Egilsson |
| 7,029,500 B2 | 4/2006 | Martin |
| 7,037,283 B2 | 5/2006 | Karason et al. |
| D523,149 S | 6/2006 | Bjarnason |
| 7,063,727 B2 | 6/2006 | Phillips et al. |
| 7,077,818 B2 | 7/2006 | Ingimundarson et al. |
| 7,094,058 B2 | 8/2006 | Einarsson |
| 7,094,212 B2 | 8/2006 | Karason et al. |
| D527,825 S | 9/2006 | Ingimundarson et al. |
| D529,180 S | 9/2006 | Ingimundarson et al. |
| 7,101,487 B2 | 9/2006 | Hsu et al. |
| 7,105,122 B2 | 9/2006 | Karason |
| 7,107,180 B2 | 9/2006 | Karason |
| 7,118,601 B2 | 10/2006 | Yasui et al. |
| 7,118,602 B2 | 10/2006 | Bjarnason |
| 7,136,722 B2 | 11/2006 | Nakamura et al. |
| D533,280 S | 12/2006 | Wyatt et al. |
| 7,144,429 B2 | 12/2006 | Carstens |
| 7,145,305 B2 | 12/2006 | Takenaka et al. |
| 7,154,017 B2 | 12/2006 | Sigurjonsson et al. |
| 7,161,056 B2 | 1/2007 | Gudnason et al. |
| 7,169,188 B2 | 1/2007 | Carstens |
| 7,169,189 B2 | 1/2007 | Bjarnason et al. |
| 7,169,190 B2 | 1/2007 | Phillips et al. |
| 7,198,071 B2 | 4/2007 | Bisbee, III et al. |
| 7,198,610 B2 | 4/2007 | Ingimundarson et al. |

(56) References Cited

U.S. PATENT DOCUMENTS

| | | |
|---|---|---|
| 7,217,060 B2 | 5/2007 | Ingimarsson |
| 7,220,889 B2 | 5/2007 | Sigurjonsson et al. |
| 7,223,899 B2 | 5/2007 | Sigurjonsson |
| 7,227,050 B2 | 6/2007 | Sigurjonsson et al. |
| 7,230,154 B2 | 6/2007 | Sigurjonsson |
| 7,235,108 B2 | 6/2007 | Carstens |
| 7,240,876 B2 | 7/2007 | Doubleday et al. |
| 7,266,910 B2 | 9/2007 | Ingimundarson |
| 7,270,644 B2 | 9/2007 | Ingimundarson |
| 7,279,009 B2 | 10/2007 | Herr et al. |
| 7,288,076 B2 | 10/2007 | Grim et al. |
| 7,295,892 B2 | 11/2007 | Herr et al. |
| RE39,961 E | 12/2007 | Petrofsky et al. |
| 7,303,538 B2 | 12/2007 | Grim et al. |
| 7,304,202 B2 | 12/2007 | Sigurjonsson et al. |
| 7,311,686 B1 | 12/2007 | Iglesias et al. |
| 7,313,463 B2 | 12/2007 | Herr et al. |
| D558,884 S | 1/2008 | Ingimundarson et al. |
| 7,335,233 B2 | 2/2008 | Hsu et al. |
| 7,347,877 B2 | 3/2008 | Clausen et al. |
| D567,072 S | 4/2008 | Ingimundarson et al. |
| 7,371,262 B2 | 5/2008 | Lecomte et al. |
| 7,377,944 B2 | 5/2008 | Janusson et al. |
| RE40,363 E | 6/2008 | Grim et al. |
| 7,381,860 B2 | 6/2008 | Gudnason et al. |
| 7,393,364 B2 | 7/2008 | Martin |
| 7,396,975 B2 | 7/2008 | Sigurjonsson et al. |
| 7,402,721 B2 | 7/2008 | Sigurjonsson et al. |
| 7,411,109 B2 | 8/2008 | Sigurjonsson et al. |
| D576,781 S | 9/2008 | Chang et al. |
| D577,828 S | 9/2008 | Ingimundarson et al. |
| 7,423,193 B2 | 9/2008 | Sigurjonsson et al. |
| 7,427,297 B2 | 9/2008 | Patterson et al. |
| 7,429,253 B2 | 9/2008 | Shimada et al. |
| 7,431,708 B2 | 10/2008 | Sreeramagiri |
| 7,431,737 B2 | 10/2008 | Ragnarsdottir et al. |
| 7,438,843 B2 | 10/2008 | Asgeirsson |
| 7,449,005 B2 | 11/2008 | Pickering et al. |
| 7,455,696 B2 | 11/2008 | Bisbee, III et al. |
| D583,956 S | 12/2008 | Chang et al. |
| 7,459,598 B2 | 12/2008 | Sigurjonsson et al. |
| 7,465,281 B2 | 12/2008 | Grim et al. |
| 7,465,283 B2 | 12/2008 | Grim et al. |
| 7,468,471 B2 | 12/2008 | Sigurjonsson et al. |
| 7,470,830 B2 | 12/2008 | Sigurjonsson et al. |
| 7,488,349 B2 | 2/2009 | Einarsson |
| 7,488,864 B2 | 2/2009 | Sigurjonsson et al. |
| D588,753 S | 3/2009 | Ingimundarson et al. |
| 7,503,937 B2 | 3/2009 | Asgeirsson et al. |
| 7,513,880 B2 | 4/2009 | Ingimundarson et al. |
| 7,513,881 B1 | 4/2009 | Grim et al. |
| D592,755 S | 5/2009 | Chang et al. |
| D592,756 S | 5/2009 | Chang et al. |
| 7,531,006 B2 | 5/2009 | Clausen et al. |
| 7,531,711 B2 | 5/2009 | Sigurjonsson et al. |
| 7,534,220 B2 | 5/2009 | Cormier et al. |
| 7,544,214 B2 | 6/2009 | Gramnas |
| 7,549,970 B2 | 6/2009 | Tweardy |
| D596,301 S | 7/2009 | Campos et al. |
| 7,578,799 B2 | 8/2009 | Thorsteinsson et al. |
| 7,581,454 B2 | 9/2009 | Clausen et al. |
| 7,597,672 B2 | 10/2009 | Kruijsen et al. |
| 7,597,674 B2 | 10/2009 | Hu et al. |
| 7,597,675 B2 | 10/2009 | Ingimundarson et al. |
| 7,618,463 B2 | 11/2009 | Oddsson et al. |
| 7,632,315 B2 | 12/2009 | Egilsson |
| 7,637,957 B2 | 12/2009 | Ragnarsdottir et al. |
| 7,637,959 B2 | 12/2009 | Clausen et al. |
| 7,641,700 B2 | 1/2010 | Yasui |
| 7,650,204 B2 | 1/2010 | Dariush |
| 7,662,191 B2 | 2/2010 | Asgeirsson |
| D611,322 S | 3/2010 | Robertson |
| 7,674,212 B2 | 3/2010 | Kruijsen et al. |
| 7,691,154 B2 | 4/2010 | Asgeirsson et al. |
| 7,696,400 B2 | 4/2010 | Sigurjonsson et al. |
| 7,704,218 B2 | 4/2010 | Einarsson et al. |
| D616,555 S | 5/2010 | Thorgilsdottir et al. |
| D616,556 S | 5/2010 | Hu |
| 7,713,225 B2 | 5/2010 | Ingimundarson et al. |
| D616,996 S | 6/2010 | Thorgilsdottir et al. |
| D616,997 S | 6/2010 | Thorgilsdottir et al. |
| D618,359 S | 6/2010 | Einarsson |
| 7,727,174 B2 | 6/2010 | Chang et al. |
| 7,731,670 B2 * | 6/2010 | Aguirre-Ollinger . A61H 1/0237 601/5 |
| 7,736,394 B2 | 6/2010 | Bedard et al. |
| 7,745,682 B2 | 6/2010 | Sigurjonsson et al. |
| D620,124 S | 7/2010 | Einarsson |
| 7,749,183 B2 | 7/2010 | Ingimundarson et al. |
| 7,749,281 B2 | 7/2010 | Egilsson |
| 7,762,973 B2 | 7/2010 | Einarsson et al. |
| 7,771,488 B2 | 8/2010 | Asgeirsson et al. |
| 7,780,741 B2 | 8/2010 | Janusson et al. |
| 7,794,418 B2 | 9/2010 | Ingimundarson et al. |
| 7,794,505 B2 | 9/2010 | Clausen et al. |
| 7,811,333 B2 | 10/2010 | Jonsson et al. |
| 7,811,334 B2 | 10/2010 | Ragnarsdottir et al. |
| D627,079 S | 11/2010 | Robertson |
| 7,833,181 B2 | 11/2010 | Cormier et al. |
| 7,842,848 B2 | 11/2010 | Janusson et al. |
| D628,696 S | 12/2010 | Robertson |
| D629,115 S | 12/2010 | Robertson |
| 7,846,213 B2 | 12/2010 | Lecomte et al. |
| 7,862,620 B2 | 1/2011 | Clausen et al. |
| 7,863,797 B2 | 1/2011 | Calley |
| 7,867,182 B2 | 1/2011 | Iglesias et al. |
| 7,867,284 B2 | 1/2011 | Bedard |
| 7,867,285 B2 | 1/2011 | Clausen et al. |
| 7,867,286 B2 | 1/2011 | Einarsson |
| 7,868,511 B2 | 1/2011 | Calley |
| 7,879,110 B2 | 2/2011 | Phillips |
| 7,891,258 B2 | 2/2011 | Clausen et al. |
| 7,892,195 B2 | 2/2011 | Grim et al. |
| D634,438 S | 3/2011 | Hu |
| D634,852 S | 3/2011 | Hu |
| 7,896,826 B2 | 3/2011 | Hu et al. |
| 7,896,827 B2 | 3/2011 | Ingimundarson et al. |
| 7,896,927 B2 | 3/2011 | Clausen et al. |
| 7,909,884 B2 | 3/2011 | Egilsson et al. |
| 7,910,793 B2 | 3/2011 | Sigurjonsson et al. |
| 7,914,475 B2 | 3/2011 | Wyatt et al. |
| 7,918,765 B2 | 4/2011 | Kruijsen et al. |
| D637,942 S | 5/2011 | Lee et al. |
| 7,935,068 B2 | 5/2011 | Einarsson |
| D640,380 S | 6/2011 | Tweardy et al. |
| D640,381 S | 6/2011 | Tweardy et al. |
| 7,955,398 B2 | 6/2011 | Bedard et al. |
| 7,959,589 B2 | 6/2011 | Sreeramagiri et al. |
| D641,482 S | 7/2011 | Robertson |
| D641,483 S | 7/2011 | Robertson et al. |
| 7,981,068 B2 | 7/2011 | Thorgilsdottir et al. |
| 7,985,193 B2 | 7/2011 | Thorsteinsson et al. |
| 7,985,265 B2 | 7/2011 | Moser et al. |
| D643,537 S | 8/2011 | Lee |
| 7,998,221 B2 | 8/2011 | Lecomte et al. |
| 8,002,724 B2 | 8/2011 | Hu et al. |
| 8,007,544 B2 | 8/2011 | Jonsson et al. |
| 1,022,480 A1 | 9/2011 | Clausen at al. |
| 8,016,781 B2 | 9/2011 | Ingimundarson et al. |
| 8,021,317 B2 | 9/2011 | Arnold et al. |
| 8,025,632 B2 | 9/2011 | Einarsson |
| 8,025,699 B2 | 9/2011 | Lecomte et al. |
| 8,026,406 B2 | 9/2011 | Janusson et al. |
| D646,394 S | 10/2011 | Tweardy et al. |
| D647,622 S | 10/2011 | Lee et al. |
| D647,623 S | 10/2011 | Thorgilsdottir et al. |
| D647,624 S | 10/2011 | Thorgilsdottir et al. |
| 1,024,593 A1 | 10/2011 | Clausen at al. |
| 8,034,120 B2 | 10/2011 | Egilsson et al. |
| 8,038,636 B2 | 10/2011 | Thorgilsdottir et al. |
| 8,043,244 B2 | 10/2011 | Einarsson et al. |
| 8,043,245 B2 | 10/2011 | Campos et al. |
| 8,048,007 B2 | 11/2011 | Roy |
| 8,048,013 B2 | 11/2011 | Ingimundarson et al. |

(56) References Cited

U.S. PATENT DOCUMENTS

| | | | |
|---|---|---|---|
| 8,048,172 B2 | 11/2011 | Jonsson et al. | |
| 8,052,760 B2 | 11/2011 | Egilsson et al. | |
| 8,057,550 B2 | 11/2011 | Clausen et al. | |
| 8,202,325 B2 | 6/2012 | Albrecht-Laatsch et al. | |
| 2001/0029400 A1 | 10/2001 | Deffenbaugh et al. | |
| 2002/0052663 A1* | 5/2002 | Herr et al. | 623/24 |
| 2002/0092724 A1 | 7/2002 | Koleda | |
| 2002/0138153 A1 | 9/2002 | Koniuk | |
| 2003/0093021 A1 | 5/2003 | Goffer | |
| 2003/0125814 A1 | 7/2003 | Paasivaara et al. | |
| 2003/0139783 A1 | 7/2003 | Kilgore et al. | |
| 2003/0163206 A1 | 8/2003 | Yasui et al. | |
| 2003/0195439 A1 | 10/2003 | Caselnova | |
| 2004/0039454 A1 | 2/2004 | Herr et al. | |
| 2004/0049290 A1 | 3/2004 | Bedard | |
| 2004/0054423 A1 | 3/2004 | Martin | |
| 2004/0064195 A1 | 4/2004 | Herr | |
| 2004/0088025 A1 | 5/2004 | Gesotti | |
| 2004/0181118 A1 | 9/2004 | Kochamba | |
| 2005/0049652 A1 | 3/2005 | Tong | |
| 2005/0059908 A1 | 3/2005 | Bogert | |
| 2005/0070834 A1* | 3/2005 | Herr et al. | 602/28 |
| 2005/0085948 A1 | 4/2005 | Herr et al. | |
| 2005/0155444 A1 | 7/2005 | Otaki et al. | |
| 2006/0004307 A1 | 1/2006 | Horst | |
| 2006/0069448 A1 | 3/2006 | Yasui | |
| 2006/0094989 A1 | 5/2006 | Scott et al. | |
| 2006/0135883 A1 | 6/2006 | Jonsson et al. | |
| 2006/0173552 A1 | 8/2006 | Roy | |
| 2006/0224246 A1 | 10/2006 | Clausen et al. | |
| 2006/0249315 A1 | 11/2006 | Herr et al. | |
| 2006/0258967 A1 | 11/2006 | Fujil et al. | |
| 2006/0276728 A1 | 12/2006 | Ashihara et al. | |
| 2007/0016329 A1* | 1/2007 | Herr et al. | 700/250 |
| 2007/0043449 A1 | 2/2007 | Herr et al. | |
| 2007/0123997 A1 | 5/2007 | Herr et al. | |
| 2007/0156252 A1* | 7/2007 | Jonsson et al. | 623/24 |
| 2007/0162152 A1 | 7/2007 | Herr et al. | |
| 2008/0114272 A1 | 5/2008 | Herr et al. | |
| 2008/0155444 A1 | 6/2008 | Pannese et al. | |
| 2008/0188907 A1* | 8/2008 | Aguirre-Ollinger . A61H 1/0237 607/48 |
| 2009/0030530 A1 | 1/2009 | Martin | |
| 2009/0171469 A1* | 7/2009 | Thorsteinsson et al. | 623/26 |
| 2009/0222105 A1 | 9/2009 | Clausen | |
| 2010/0025409 A1 | 2/2010 | Hunter | |
| 2010/0114329 A1 | 5/2010 | Casler et al. | |
| 2010/0179668 A1* | 7/2010 | Herr et al. | 623/51 |
| 2010/0312363 A1 | 12/2010 | Herr et al. | |
| 2011/0210626 A1* | 9/2011 | Schmidt | 310/46 |

FOREIGN PATENT DOCUMENTS

| | | |
|---|---|---|
| WO | WO-2004017872 | 3/2004 |
| WO | WO-2004019832 | 3/2004 |
| WO | WO-2006110895 | 10/2006 |
| WO | WO-2009082249 | 7/2009 |
| WO | WO-2010025409 | 3/2010 |
| WO | WO-2010027968 | 3/2010 |

OTHER PUBLICATIONS

Abul-haj, C. and Hogan, N., "Functional assessment of control systems for cybernetic elbow prostheses. Part I, Part II," IEEE Transactions on Biomedical Engineering, vol. 37, No. 11, Nov. 1990, Cambridge, MA, pp. 1025-1047.

Akazawa, K., et. al, "Biomimetic EMG prosthesis-hand," Proceedings of the 18th Annual International Conference of the IEEE Engineering in Medicine and Biology Society, vol. 2, Oct. 1996, Amsterdam, Netherlands, pp. 535-536.

Aminian, "Estimation of Speed and Incline of Walking Using Neural Network," IEEE Transactions on Biomedical Engineering, vol. 44, No. 3, Jun. 1995, pp. 743-746.

Anderson, F. and Pandy M., "Dynamic optimization of human walking," Journal of Biomechanical Engineering, vol. 123, Oct. 2001, pp. 381-390.

Andrews, et al., "Hybrid FES Orthosis incorporating closed loop control and sensory feedback," J. Biomed Eng., vol. 10, Apr. 1988, pp. 189-195.

Arakawa, T. and Fukuda, T., "Natural motion generation of biped locomotion robot using hierarchical trajectory generation method consisting of GA, EP layers," Proceedings of the 1997 IEEE International Conference on Robotics and Automation, Apr. 1997, Albuquerque, NM, pp. 211-216.

Au., et. al., "Powered Ankle-Foot Prosthesis for the Improvement of Amputee Ambulation," Proceedings of the 29th Annual International Conference of the IEEE, Aug. 2007, Lyon, France, pp. 3020-3026.

Au, S., "An EMG-position controlled system for an active ankle-foot prosthesis: an initial experimental study," Proc. of the 2006 IEEE International Conference on Rehabilitation Robotics, Jul. 2005, Chicago, IL, pp. 375-379.

Au, S. and Herr H., "Initial experimental study on dynamic interaction between an amputee and a powered ankle-foot prosthesis," Workshop on Dynamic Walking: Mechanics and Control of Human and Robot Locomotion, May 2006, Ann Arbor, MI, p. 1.

Au, S., et al. "An ankle-foot emulation system for the study of human walking biomechanics," Proc. of the 2006 IEEE Int. Conf. on Robotics and Automation, May 2006, Orlando, FL, pp. 2939-2945.

Au, S., et. al., "Biomechanical design of a powered ankle-foot prosthesis," Proc. of the 2007 IEEE Int. Conf. on Rehabilitation Robotics, Jun. 2007, Noordwijk, Netherlands, pp. 298-303.

Au, S., et. al., "Powered ankle-foot prosthesis to assist level-ground and stair-descent gaits," Neural Networks, vol. 21, No. 4, Mar. 2008, pp. 654-666.

Au, S., et. al., "Powered Ankle-foot Prosthesis Improves Walking Metabolic Economy," IEEE Trans. on Robotics, vol. 25, No. 1, Feb. 2009, pp. 51-66.

Barth, D., et. al., "Gait analysis and energy cost of below-knee amputees wearing six different prosthetic feet," Journal of Prosthetics & Orthotics, vol. 4, No. 2, Winter, 1992, pp. 63-75.

Baten, et al., "Inertial Sensing in Ambulatory back load Estimation," 18 Annual International Conferences of IEEE Engineering in Medicine and Biology Society, Amsterdam 1996, pp. 497-498.

Bateni, H. and Olney S., "Kinematic and kinetic variations of below-knee amputee gait," Journal of Prosthetics & Orthotics, vol. 14, No. 1, Mar. 2002, pp. 2-13.

Blaya, J. and Herr, H, "Adaptive control of a variable-impedance ankle-foot orthosis to assist drop-foot gait," IEEE Transactions on Neural Systems and Rehabilitation Engineering, vol. 12, No. 1, Mar. 2004, pp. 24-31.

Blaya, J.A., and Herr, H., "Adaptive Control of a Variable-Impedance Ankle-Foot Orthosis to Assist Drop Foot Gait," Artificial Intelligence Lab and Harvard-MIT Division Health Sciences and Technology, Boston, MA, 30 pages.

Blaya, J.A., et al., "Active Ankle Foot Orthoses (AAFO)," http://www.ai,mit.edu. Artificial Intelligence Laboratory, Massachusetts Institute of Technology, Cambridge, Massachusetts, 3 pages.

Blaya, J.A., "Force-Controllable Ankle Foot Orthosis (AFO) to Assist Drop Foot Gait," submitted to the Department of Mechanical Engineering, Massachusetts Institute of Technology, Cambridge, Massachusetts (Feb. 2003). 88 pages.

Blickhan, R., "The spring-mass model for running and hopping," J of Biomech. Feb. 22, 1989, Great Britain, pp. 1217-1227.

Bortz, "A New Mathematical Formulation for Strapdown Inertial Navigation," IEEE Transactions of Aerospace and Electronic Systems, vol. AES-7, No. 1, Jan. 1971, p. 61-66.

Brockway, J., "Derivation of formulae used to calculate energy expenditure in man," Human Nutrition Clinical Nutrition, vol. 41, Nov. 1987, pp. 463-471.

Brown, R., "On the nature of the fundamental activity of the nervous centres: together with an analysis of the conditioning of rhythmic activity in progression, and a theory of the evolution of function in the nervous system," J Physiol, vol. 48, No. 1, Mar. 1914, pp. 18-46.

(56) References Cited

OTHER PUBLICATIONS

Chang, et al., Ischemic Colitis and Complications of Constipation Associated with the use of Alosetron Under a Risk Management Plan: Clinical Characteristics, Outcomes, and Incidences the Americal Journal of Gastronenterology, vol. 105, No. 4, Apr. 2010, pp. 866-875.
Chu, A., Kazerooni, H. and Zoss, A., "On the Biomimetic Design of the Berkeley Lower Extremity Exoskeleton (BLEEX)," Proceedings of the 2005 IEEE International Conference on Robotics and Automation, Apr. 2005, Barcelona, Spain, pp. 4356-4363.
Colborne, G. R., S. Naumann, P. E. Langmuir, and D. Berbrayer, "Analysis of mechanical and metabolic factors in the gait of congenital below knee amputees," Am. J. Phys. Med. Rehabil., vol. 92, pp. 272-278, Oct. 1992.
Collins, et al., "Controlled Energy Storage and Return Prosthesis Reduces Metabolic cost of Walking," ASB 29th Annual Meeting, Cleveland, Ohio, Jul. 31-Aug. 5, 2005, 1 page.
Collins, et al., "Supporting Online Material for Efficient bipedal robots based on passivedynamic walkers," Mechanical Engineering, University of Michigan, Feb. 2005, Ann Arbor, MI, pp. 1-8.
Crago P., et. al., "New Control Strategies for neuroprosthetic systems," Journal of Rehabilitation Research and Development, vol. 33, No. 2, Apr. 1996, pp. 158-172.
Daley, M.A., Felix, G., Biewener, A. A., 2007. Running stability is enhanced by a proximodistal gradient in joint neuromechanical control. J Exp Bioi 210 (Pt 3), Nov. 2006, pp. 383-394.
Dapena, J. and McDonald, C., "Three-dimensional analysis of angular momentum in the hammer throw," Med. Sci. in Sports Exerc., vol. 21, No. 2, Apr. 1989, pp. 206-220.
Dietz, V., "Proprioception and locomotor disorders," Nat Rev Neurosci, vol. 3, Oct. 2002, pp. 781-790.
Dietz, V., "Spinal Cord Pattern Generators for Locomotion," download Feb. 6, 2012, http://www.Clinph-journal.com/article/PIIS1388245703001202/fulltext, 12 pages.
Doerschuk, et. al., "Upper extremity limb function discrimination using EMG signal analysis," IEEE Transactions on Biomedical Engineering. vol. 30., No. 1., Jan. 1983, pp. 18-28.
Doke, J., et. al., "Mechanics and energetics of swinging the human leg," The Journal of Experimental Bioloqy, vol. 208, Feb. 2005, pp. 439-445.
Dollar, et al., "Lower Extremity Exoskeletions and Active Orthoses: Challenges and State-of-the-Art," IEEE Transactions on Robotics, vol. 24, No. 1, Feb. 2008, 15 pages.
Donelan, J., et. al., "Force regulation of ankle extensor muscle activity in freely walking cats," J Neurophysiol, vol. 101, No. 1, Nov. 2008, pp. 360-371.
Donelan, J., et. al., "Mechanical work for step-to-step transitions is a major determinant of the metabolic cost of human walking," J. Exp. Bioi., vol. 205, Dec. 2002, pp. 3717-3727.
Donelan, J., et. al. "Simultaneous positive and negative external mechanical work in human walking," Journal of Biomechanics, vol. 35, Jan. 2002, pp. 117-124.
Drake, C., "Ankle & Foot Splints or Orthoses," HemiHelp, Information Sheet 13 Last updated Jun. 2009, 5 pages.
Drake, C., "Ankle & Foot Splints or Orthoses (AFOs)," HemiHelp, Last updated Jun. 2009, 8 pages.
Drake, C., "Foot & Ankle Splints or Orthoses," HemiHelp Information Sheet, London, United Kingdom, 3 pages, www.hemihelp.org.uk/leaflets/hbleaflets90.htm.
Eilenberg, M., "A Neuromuscular-Model Based Control Strategy for Powered Ankle-Foot Prostheses," Master's Thesis, Massachusetts Institute of Technology, Cambridge, Mass., 2009.
Ekeberg, 0. and Grillner, S., "Simulations of neuromuscular control in lamprey swimming," Philos Trans R Soc Land B Bioi Sci, vol. 354, May 1999, pp. 895-902.
Ekeberg, 0. and Pearson, K., "Computer simulation of stepping in the hind legs of the cat: an examination of mechanisms regulating the stance-to-swing transition," J Neurophysiol, vol. 94, No. 6, Jul. 2005, pp. 4256-4268.

Endo, K., et. al., "A quasi-passive model of human leg function in level-ground walking," Proc. of 2006 IEEE/RSJ International Conference on Intelligent Robots and Systems (IROS), Oct. 2006, Beijing, China, pp. 4935-4939.
Eppinger, S. Seering W., "Three dynamic problems in robot force control," IEEE Transactions on Robotics and Automation, vol. 8, No. 6, Dec. 1992, pp. 751-758.
Esquenazi, A. and DiGiacomo, R., "Rehabilitation After Amputation," Journ Am Podiatr Med Assoc, vol. 91, No. 1, Jan. 2001, pp. 13-22.
Farley, C. and McMahon, T., "Energetics of walking and running: insights from simulated reduced-gravity experiments," The American Physiological Society, Dec. 1992, pp. 2709-2712.
Farry, K. A., et al., "Myoelectric teleoperation of a complex robotic hand," IEEE Transactions on Robotics and Automation. vol. 12, No. 5, Oct. 1996, pp. 775-788.
Featherstone, R., 1987, "Robot Dynamic Algorithms", Boston, Mass., Kluwer Academic Publishers, pp. 155-172.
Fite, K., et. al., "Design and Control of an Electrically Powered Knee Prosthesis," Proc. of 2007 IEEE 10th International Conference on Rehabilitation Robotics (ICORR), Jun. 2007, pp. 902-905.
Flowers, W. "A Man-Interactive Simulator System for Above-Knee Prosthetic Studies," Ph.D. thesis, Massachusetts of Institute Technology, Department of Mechanical Engineering. Jul. 10, 1973.
Fod, A., et. al., "Automated Derivation of Primitives for Movements Classification," Autonomous Robots, vol. 12, No. 1, Jan. 2002, pp. 39-54.
Frigon, A. and Rossignol, S., "Experiments and models of sensorimotor interactions during locomotion," Bioi Cybern, vol. 95, No. 6, Nov. 2006, pp. 607-627.
Fujita K, et. al., "Joint angle control with command filter for human ankle movement using functional electrical stimulation," Proc. of IEEE Ninth Annual Conference for the Engineering in Medicine and Biology Society, Nov. 1987, Boston, MA, pp. 1719-1720.
Fukuda, 0. et al., "A human-assisting manipulator teleoperated by EMG signals and arm motions," IEEE Transactions on Robotics and Automation. vol. 19, No. 2, Apr. 2003, pp. 210-222.
Gates, D., "Characterizing ankle function during stair ascent, descent, and level walking for ankle prosthesis and orthosis design," Masters thesis, Boston University, 2004, pp. 1-82.
Geiritsen, K., et. al., "Direct dynamics simulation of the impact phase in heel-toe running," J. Biomech., vol. 28, No. 6, Jun. 1995, Great Britain, pp. 661-668.
Geyer, H., et. al., "Compliant leg behaviour explains the basic dynamics of walking and running," Proc. R. Soc. Cond. B 273, Aug. 2006, pp. 2861-2867.
Geyer, H., et. al., "Positive force feedback in bouncing gaits?," Proceedings of Royal Society B-Biological Sciences, vol. 270, No. 1529, Aug. 2003, pp. 2173-2183, 2003.
Geyer, H. and Herr H., "A muscle-reflex model that encodes principles of legged mechanics predicts human walking dynamics and muscle activities," IEEE Transactions on Neural Systems and Rehabilitations Engineering, vol. 18, No. 3, Jun. 2010, pp. 263-273.
Ghigliazza, R., et. al., "A simply stabilized running model," SIAM J. Applied. Dynamical Systems, vol. 2, No. 2, May 2004, pp. 187-218.
Godha, el al., "Integrated GPS/INS System for Pedestrian Navigation in a Signal Degraded Environment," ION GNSS, Sep. 2006, Fort Worth, TX, pp. 1-14.
Goswami, A., "Postural stability of biped robots and the foot-rotation indicator (FRI) point," International Journal of Robotics Research, vol. 18, No. 6, Jun. 1999, pp. 523-533.
Goswami, A. and Kallem, V., "Rate of change of angular momentum and balance maintenance of biped robots," Proceedings of the 2004 IEEE International Conference on Robotics and Automation, Apr. 2004, New Orleans, La., pp. 3785-3790.
Graupe, D., et al., "A microprocessor system for multifunctional control of upper-limb prostheses via myoelectric signal identification," IEEE Transaction on Automatic Control. vol. AC-23, vol. 4, Aug. 1978, pp. 538-544.
Gregoire, L., and et al, "Role of mono- and bi-articular muscles in explosive movements," International Journal of Sports Medicine 5, 614-630. Dec. 1984.

(56) References Cited

OTHER PUBLICATIONS

Grillner, S. and Zangger, P., "On the central generation of locomotion in the low spinal cat," Exp Brain Res, vol. 34, No. 2, Jan. 1979, pp. 241-261.
Grimes, D. L., "An active multi-mode above-knee prosthesis controller," Ph.D. Thesis, Massachusetts Institute of Technology, Jul. 20, 1979.
Gu, W., "The Regulation of Angular Momentum During Human Walking," Undergraduate Thesis, Massachusetts Institute of Technology, Physics Department, Jun. 2003, pp. 2-48.
Gunther, M., et. al., "Human leg design: optimal axial alignment under constraints," J. Math. Bioi., vol. 48, Mar. 2004, pp. 623-646.
Gunther, M. and Ruder, H., "Synthesis of two-dimensional human walking: a test of the Amodel," Bioi. Cybern., vol. 89, May 2003, pp. 89-106.
Hanafusa et al., "A Robot Hand with Elastic Fingers and Its Application to Assembly Process," pp. 337-359, Robot Motion, Brady et al., MIT Press, Cambridge, MA, 1982.
Hansen, A. H., Childress, D. S., Miff, S.C., Gard, S. A., Mesplay, K. P., "The human ankle during walking: implication for the design of biomimetic ankle prosthesis," Journal of Biomechanics, vol. 37, No. 10, Oct. 2004, pp. 1467-1474.
Hayes et al., "Leg Motion Analysis During Gait by Multiaxial Accelerometry: Theoretical Foundations and Preliminary Validations," Journal of Biomechanical Engineering, vol. 105, Aug. 1983, pp. 283-289.
Heglund, N., "A Simple Design for a Force-Plat to Measure Ground Reaction Forces," J. Exp. Bioi., vol. 93, Aug. 1981, pp. 333-338.
Herr, H. and McMahon, T.,"A trotting horse model," Int. J. Robotics Res., vol. 19, No. 6, Jun. 2000, pp. 566-581.
Herr, H. and Popovic, M., "Angular momentum regulation in human walking," J. Exp. Bioi., vol. 211, Feb. 2008, pp. 467-481.
Herr, H. and Wilkenfeld A., "User-adaptive control of a magnetorheologicalprosthetic knee," Industrial Robot: An International Journal, vol. 30, No. 1, 2003, pp. 42-55.
Herr, H., et. al, "A model of scale effects in mammalian quadrupedal running," J Exp Bioi 205 (Pt 7), Apr. 2002, pp. 959-967.
Heyn et al., "The Kinematice of the Swing Phase Obtained from Accelerometer and Gyroscope Measurements," 18th Annual International Conference of the IEEE Engineering in Medicine and Biology Society, Nov. 1996, Amsterdam, Netherlands, pp. 463-464.
Hill, V., "The heat of shortening and the dynamic constants of muscle," Proceedings of the Royal Society London B, vol. 126, No. 843, Oct. 1938, pp. 136-195.
Hirai, K., et al., "The development of Honda humanoid robot," Proceedings on IEEE/RSJ International Conference on Intelligent Robots and Systems, May 1998, Leuven, Belgium, pp. 1321-1326.
Hitt, J., R. Bellman, M. Holgate, T. Sugar, and K. Hollander, "The sparky (spring ankle with regenerative kinetics) projects: Design and analysis of a robotic transtibial prosthesis with regenerative kinetics," in Proc. IEEE Int. Conf. Robot. Autom., Orlando, Fla., pp. 2939-2945, Sep. 2007.
Hof. A., et. al., "Calf muscle moment, work and efficiency in level walking; role of series elasticity," Journal of Biomechanics, vol. 16, No. 7, Sep. 1983, pp. 523-537.
Hofbaur, M. and Williams, B., "Hybrid Diagnosis with Unknown Behavioral Modes", Proceedings of the 13.sup.th International Workshop on Principles of Diagnosis (DX02), May 2002, pp. 1-10.
Hofbaur, M. and Williams, B., "Mode Estimation of Probabilistic Hybrid Systems", HSSC 2002, LNCS 2289, Mar. 25, 2002, pp. 253-266.
Hofmann, A., et. al., "A Sliding Controller for Bipedal Balancing Using Integrated Movement of Contact and Non-Contact Limbs," Proceedings of the IEEE/RSJ International Conference on Intelligent Robots and Systems, Sep. 2004, Sendai, Japan, pp. 1952-1959.
Hofmann, A., et. al., "Robust Execution of Bipedal Walking Tasks from Biomechanical Principles," Doctor of Philosophy at the Massachusetts Institute of Technology, Jan. 2006, 407 pages.

Hogan, N and Buerger S., "Impedance and Interaction Control," Robotics and Automation Handbook, CRC Press, Jun. 2004, pp. 19.1-19.24.
Hogan, N. (1976) A review of the methods of processing EMG for use as a proportional control signal. Biomedical Engineering. pp. 81-86.
Hogan, N., "Impedance Control: An Approach to Manipulation: Part I—Theory," Journal of Dynamic Systems, Measurement, and Control, vol. 107, Mar. 1985, pp. 1-7.
Hogan, N., "Impedance Control: An Approach to Manipulation: Part II—Implementation, " Journal of Dynamic Systems, Measurement , and Control, 107:8-16, (1985).
Hogan, N., Impedance Control: An Approach to Manipulation: Part III—Application, Journal of Dynamics Systems, Measurement, and Control, 107:17-24, (1985).
Hogan, N., "Impedance Control: An Approach to Manipulation," Dept. of Mechanical Engineering and Laboratory of Manufacturing and Productivity, Massachusetts Institute of Technology, Cambridge MA, pp. 304-313, (Jun. 1984).
Hollander, K. W., T. G. Sugar, and D. E. Herring, "Adjustable robotic tendon using a 'Jack Spring' .TM.," Proceedings on IEEE International Conference on Rehabilitation Robotics, Chicago, pp. 113-118, Jun. 28, 2005.
Howard, "Joint and Actuator Design for Enhanced Stability in Robotic Force Control," Ph.D. thesis, Massachusetts Inst. Of Technology, Dept. of Aeronautics and Astronautics, Sep. 19, 1990.
Huang, H. and Chen. C., "Development of a myoelectric discrimination system for a multi-degree prosthetic hand," Proceeding of the 1999 IEEE International Conference on Robotics and Automation, May 1999, Detroit, MI, pp. 2392-2397.
Huang, Q., "Planning walking patterns for a biped robot," IEEE Transactions on Robotics and Automation, vol. 17, No. 3, Jun. 2001, pp. 280-289.
Hultborn, H., Spinal reflexes, mechanisms and concepts: from Eccles to Lundberg and beyond, Prog Neurobiol, vol. 78, Feb. 2006, pp. 215-232.
Ijspeert, A. J., 2008, "Central pattern generators for locomotion control in animals and robots: a review," Neural Netw, vol. 21, No. 4, May 2008, pp. 642-653.
Ijspeert, A., et. al., "From swimming to walking with a salamander robot driven by a spinal cord model," Science, vol. 315, No. 5817, Mar. 2007, pp. 1416-1420.
International Search Report and Written Opinion for PCT/US2009/055600 mailed Apr. 29, 2010 (23 pages).
International Search Report and Written Opinion for PCT/US2010/047279 mailed Jan. 19, 2011 (11 pages).
International Search Report and Written Opinion for PCT/US2011/031105 mailed Oct. 11, 2011 (16 pages).
International Search Report for PCT/US2012/020775 mailed Jun. 1, 2012 (6 pages).
International Search Report for PCT/US2012/021084 mailed Aug. 1, 2012 (3 pages).
International Search Report for PCT/US2012/022217 mailed May 31, 2012 (6 pages).
Ivashko, D., et. al, "Modeling the spinal cord neural circuitry controlling cat hindlimb movement during locomotion," Neurocomputing, vol. 52-54, Mar. 2003, pp. 621-629.
Johansson, J., et al., "A clinical comparison of variable damping and mechanically passive prosthetic knee devices," American Journal of Physical Medicine & Rehabilitation, vol. 84, No. 8, Aug. 2005, pp. 563-575.
Johnson, C. and Lorenz R., "Experimental identification of friction and its compensation in precise, position controlled mechanisms," IEEE Trans. on Industry Applications, vol. 28, No. 6, Dec. 1992, pp. 1392-1398.
Jonic S, et. al., "Three machine learning techniques for automatic determination of rules to control locomotion," IEEE Trans Biomed Eng, vol. 46, No. 3, Mar. 1999, pp. 300-310.
Kadaba, M., et. al., "Measurement of lower extremity kinematics during level walking," J. Orthop. Res., vol. 8, May 1990, pp. 383-392.

(56) References Cited

OTHER PUBLICATIONS

Kadaba, M., et. al., "Repeatability of kinematic, kinetic, and electromyographic data in normal adult gait," J. Orthop. Res., vol. 7, Nov. 1989, pp. 849-860.
Kajita, K., et. al., "Biped walking on a low friction floor," Proceedings of the 2004 IEEE/RSJ International Conference on Intelligent Robots and Systems, Oct. 2004, Sendai, Japan., pp. 3546-3551.
Kajita, S., et. al., "A Hop towards Running Humanoid Biped," Proceedings of the 2004 IEEE International Conference on Robotics and Automation, Apr. 2004, New Orleans, La., pp. 629-635.
Kajita, S., et. al., "Resolved Momentum Control: Humanoid Motion Planning based on the Linear and Angular Momentum," Proceedings of the 2003 IEEE/RSJ International Conference on Intelligent Robots and Systems, Oct. 2003, Las Vegas, Nev., pp. 1644-1650.
Kaneko, K., et al., "Humanoid robot HRP-2," Proc. IEEE Int. Conf. on Robotics and Automation, Apr. 2004, New Orleans, La., pp. 1083-1090.
Kapti, A. and Yucenur M., "Design and control of an active artificial knee joint," Mechanism and Machine Theory, vol. 41, Apr. 2006, pp. 1477-1485.
Katie, D. and Vukobratovic, M., "Survey of intelligent control techniques for humanoid robots," Journal of Intelligent and Robotics Systems, vol. 37, Jun. 2003, pp. 117-141.
Kerrigan, D, et. al., "A refined view of the determinants of gait: significance of heel rise," Arch. Phys. Med. Rehab., vol. 81, Aug. 2000, pp. 1077-1080.
Kerrigan, D, et. al., "Quantification of pelvic rotation as a determinant of gait," Arch. Phys. Med. Rehab., vol. 82, Feb. 2001, pp. 217-220.
Khatib, 0., et. al., "Coordination and decentralized cooperation of multiple mobile manipulators," Journal of Robotic Systems, vol. 13, No. 11, Nov. 1996, pp. 755-764.
Khatib, 0., et. al., "Whole body dynamic behavior and control of human-like robots," International Journal of Humanoid Robotics, vol. 1, No. 1, Mar. 2004, pp. 29-43.
Kidder, et al., "A System for the Analysis of Foot and Ankle Kinematics During Gait," IEEE Transactions on Rehabilitation Engineering, vol. 4, No. 1, Mar. 1996, pp. 25-32.
Kim, et al., "Realization of Dynamic Walking for the Humaniod Robot Platform KHR-1," Advanced Robotics, vol. 18, No. 7, pp. 749-768, (2004).
Kirkwood C, et. al., "Automatic detection of gait events: a case study using inductive learning techniques.," J Biomed Eng, vol. 11, Nov. 1989, pp. 511-516.
Kitayama, I., Nakagawa N, Amemori K, "A microcomputer controlled intelligent A/K prosthesis," Proceedings of the 7th' World Congress of the International Society for Prosthetics and Orthotics, Chicago. Jun. 28, 1992.
Klute, et al., Artificial Muscles: Actuators for Lower Limb Prostheses, Abstract in: Proceedings of the 2nd Annual Meeting of the VA rehabilitation Research and Development Service, Feb. 20-22, 2000, p. 107.
Klute, et al., "Artificial Muscles: Actuators for Biorobotic Systems," The International Journal of Robotics Research, vol. 21, No. 4, Apr. 2002, pp. 295-309.
Klute, et al., "Artificial Tendons: Biomechanical Design Properties for Prosthetic Lower Limbs," Chicago 2000 World Congress on Medical Physics and Biomedical Engineering, Chicago on Jul. 24-28, 2000, 4 pages.
Klute, et al., Intelligent Transtibial Prostheses with Muscle-Like Actuators,: 2002 American Physiological Society Intersociety Meeting: The Power of Comparative Physiology: Evolution, Integration, and Applied, 1 page.
Klute, et al., "Lower Limb Prostheses Powered by Muscle-Like Pneumatic Actuator," Submitted to Oleodinamica e Pneumatica, Publishe Tecniche Nuove, Milamo, Italy, Mar. 15, 2000, 6 pages.
Klute, et al., "McKibben Artificial Muscles: Pneumatic Actuators with Biomechanical Intelligence," IEEE/ASME 1999 International Conference on Advanced Intelligent Mechatronics, Atlanta, GA, Sep. 19-22, 1999, pp. 221-226.
Klute, et al., "Muscle-Like Pneumatic Actuators for Below-Knee Prostheses," Actuator2000:7th International Conference on New Actuators, Bremen, Germany on Jun. 9-21, 2000, pp. 289-292.
Klute et al., "Powering Lower Limb Prosthestics with Muscle-Like Actuators," Abstract in: Proceeding of the 1st Annual Meeting of the Va Rehabilitation Research and Development Service, "Enabling Veterans: Meeting the Challenge of Rehabilitation in the Next Millennium," Washington, D.C., Oct. 1-3, 1998, p. 52.
Klute, et al., "Variable Stiffness Prosthesis for Transtibial Amputees," Dept of Veteran Affairs, Seattle, WA USA, 2 pages.
Klute, G., et. al., "Mechanical properties of prosthetic limbs adapting to the patient," Journal of Rehabilitation Research and Development, vol. 38, No. 3, May 2001, pp. 299-307.
Koganezawa, K. and Kato, 1., "Control aspects of artificial leg," IFAC Control Aspects of Biomedical Engineering, 1987, pp. 71-85.
Kondak, K. and Hommel, G., "Control and online computation of stable movement for biped robots," Proc. of the 2003 IEEE/RSJ International Conference on Intelligent Robots and Systems (IROS), Oct. 2003, Las Vegas, Nev., pp. 874-879.
Kostov A., et. al., "Machine learning in control of functional electrical stimulation (FES) systems for locomotion," IEEE Trans on Biomed Eng, vol. 42, No. 6, Jun. 1995, pp. 541-551.
Kuo, A., "A simple model of bipedal walking predicts the preferred speed-step length relationship," Journal of Biomechanical Engineering, vol. 123, Jun. 2001, pp. 264-269.
Kuo, A., "Energetics of actively powered locomotion using the simplest walking model," Journal of Biomechanical Engineering, vol. 124, Feb. 2002, pp. 113-120.
LaFortune, "Three-Dimensional Acceleration of the Tibia During Walking and Running," J. Biomechanics, vol. 24, No. 10, 1991, pp. 877-886.
LeBlanc, M. and Dapena, J., "Generation and transfer of angular momentum in the javelin throw," Presented at the 20th annual meeting of the American Society of Biomechanics, Oct. 1996, Atlanta, Ga., pp. 17-19.
Li, C., et al. (Jun. 25, 2006) Research and development of the intelligently-controlled prosthetic ankle joint. Proc. of IEEE Int. Conf. on Mechatronics and Automation. Luoyang, China, pp. 1114-1119.
Liu, X., Low, K. H., Yu, H. Y., Sep. (2004) 'Development of a Lower Extremity Exoskeleton for Human performance Enhancement', IEEE Conf. on Intelligent Robots and Systems, Sendai, Japan.
Light, et. al., Skeletal Transients on Heel Strike in Normal Walking With Different Footwear. J. Biomechanics vol. 13, pp. 477-480.
Lloyd R. and Cooke C., "Kinetic changes associated with load carriage using two rucksack designs," Ergonomics, vol. 43, No. 9, Sep. 2000, pp. 1331-1341.
Luinge, "Inertial Sensing of Human Movement," Twente University Press, ISBN 9036518237, 2002, pp. 1-80.
Lundberg, A., Oct. 19, 1968. Reflex control of stepping. In: The Nansen memorial lecture V, Oslo: Universitetsforlaget, 5-42.
Macfarlane, P., "Gait comparisons for below-knee amputees using a flex-foot versus a conventional prosthetic foot," Journal of Prosthetics & Orthotics, vol. 3, No. 4, Summer, 1991, pp. 150-161.
Maganaris, C., "Force-length characteristics of in vivo human skeletal muscle," Acta Physiol. Scand., vol. 172, Aug. 2001, pp. 279-285.
Maganaris, C., "Force-length characteristics of the in vivo human gastrocnemius muscle," Clin. Anal., vol. 16, May 2003, pp. 215-223.
Martens, W.L.J., "Exploring the Information Content and Some Applications of Body Mounted Piezo-Resistive Accelerometers," in: P.H. Veltink and R.C. van Lummel (eds.), Dynamic Analysis using Body Fixed Sensors, ISBN 90-9007328-0, 1994, pp. 8-11.
Maufroy, C., Towards a general neural controller for quadrupedal locomotion, Neural Netw, vol. 21, No. 4, Apr. 2008, pp. 667-681.
Mayagoitia R., et al., "Accelerometer and rate gyroscope measurement of kinematics: an inexpensive alternative to optical motion analysis systems," Journal of Biomechanics, vol. 35, Apr. 2002, pp. 537-542.

(56) References Cited

OTHER PUBLICATIONS

McFadyen, B. and Winter, D., "An integrated biomechanical analysis of normal stair ascent and descent," Journal of Biomechanics, vol. 21, No. 9, 1988, Great Britain, pp. 733-744.
McGeer T., "Passive Dynamic Walking," International Journal of Robotics, vol. 9, No. 2, May 1988, pp. 62-82.
McGeer, T., "Principles of walking and running," Advances in Comparative and Environmental Physiology, vol. 11, Ch. 4, Apr. 1992, pp. 113-139.
Mcintosh, A., et. al., "Gait dynamics on an inclined walkway," Journal of Biomechanics, vol. 39, Sep. 2005, pp. 2491-2502.
McMahon, T., "The mechanics of running: how does stiffness couple with speed?," J. of Biomecb., vol. 23, 1990, pp. 65-78.
McMahon, T., et. al., "Groucho Running," Journal of Applied Physiology, vol. 62, No. 6, Jun. 1987, pp. 2326-2337.
Minassian, K., et. al., "Human lumbar cord circuitries can be activated by extrinsic tonic input to generate locomotor-like activity," Hum. Mov. Sci., vol. 26, Mar. 2007, pp. 275-295.
Mochon, S., et. al., "Ballistic walking," Journal of Biomechanics, vol. 13, Dec. 1980, pp. 49-57.
Molen, N., "Energy/speed relation of below-knee amputees walking on motor-driven treadmill," Int. Z. Angew. Physio, vol. 31, Mar. 1973, pp. 173.
Morris, "Accelerometry—A Technique for the Measurement of Human Body Movements," J. Biomechanics, vol. 6, Nov. 1973, pp. 729-736.
Muraoka, T., et. al, "Muscle fiber and tendon length changes in the human vastus lateralis during slow pedaling," J. Appl. Physiol., vol. 91, Nov. 2001, pp. 2035-2040.
Nakagawa A., "Intelligent Knee Mechanism and the Possibility to Apply the Principle to the Other Joints," Proceedings of the 20th Annual International Conference of the IEEE Engineering in Medicine and Biology Society, Vo. 20, No. 5, Oct. 1998, pp. 2282-2287.
Neal R. and Hinton G., "A view of the EM algorithm that justifies incremental, sparse, and other variants," In Michael I. Jordan (editor), Learning in Graphical Models, 1999, Cambridge, MA, pp. 1-14.
Ng, et al., "Fuzzy Model Identification for Classification of Gait Events in Paraplegics," IEEE Transactions on Fuzzy Systems, vol. 5, No. 4, Nov. 1997, pp. 536-544.
Nielsen, D., et. al., "Comparison of energy cost and gait efficiency during ambulation in below-knee amputees using different prosthetic feet—a preliminary report," Journal of Prosthetics & Orthotics, vol. 1, No. 1, 1989, pp. 24-29.
Oda, T, Ketal., 2005, "In vivo length-force relationships on muscle fiver and muscle tendon complex in the tibialis anterior muscle." Int. J. Sport and Health Sciences 3, 245-252.
Ogihara, N. and Yamazaki, N., "Generation of human bipedal locomotion by a bio-mimetic neuro-musculo-skeletal model," Bioi Cybern, vol. 84, No. 1, Jan. 2001, pp. 1-11.
Palmer, M., "Sagittal plane characterization of normal human ankle function across a range of walking gait speeds," Master's Thesis, MIT, Feb. 2002, Cambridge, MA, pp. 1-71.
Paluska, D., and Herr, H., "Series Elasticity and Actuator Power Ouput," Proceedings of the 2006 IEEE International Conference on Robotics and Automation, May 2006, Orlando, FL, pp. 1830-1833.
Paluska, D., and Herr, H., "The effect of series elasticity on actuator power and work output: implications for robotic and prosthetic joint design," Robotics and Autonomous Systems, vol. 54, Jun. 2006, pp. 667-673.
Pang, M., et. al., "The initiation of the swing phase in human infant stepping: importance of hip position and leg loading," J Physiol, vol. 528, No. 2, Oct. 2000, pp. 389-404.
Pasch, K. A., and W. P. Seering, "On the drive systems for high performance machines," AMSE J. Mechanisms, Transmissions, and Automation in Design vol. 106, pp. 102-108, Mar. 1984.
Paul, C., et. al., "Development of a human neuro-musculo-skeletal model for investigation of spinal cord injury," Bioi Cybern, vol. 93, No. 3, Aug. 2005, pp. 153-170.

Pearson, K., "Generating the walking gait: role of sensory feedback," Prog Brain Res, vol. 143, 2004, pp. 123-129.
Pearson, K., et. al., "Assessing sensory function in locomotor systems using neuro-mechanical simulations," Trends Neurosci, vol. 29, No. 11, Nov. 2006, pp. 625-631.
Perry, Gait Analysis: Normal and Pathological Function, New Jersey: SLACK Inc.; 1992, Book Review, 1 page.
Perry, J. and S. Shanfield, "Efficiency of dynamic elastic response prosthetic feet," Journal of Rehabilitation Research and Development, vol. 30, No. 1, 1993 pp. 137-143.
Petrofshy et al., "Feedback Control System for Walking in Man," Comput. Bioi. Med., vol. 14, No. 2, Mar. 1984, pp. 135-149.
Pfeffer et al., "Experiments with a Dual-Armed, Cooperative, Flexible-Drivetrain Robot System," Proc. 1993 IEEE Int. Conf. on Robotics & Automation, vol. 3, pp. 601-608, May 5, 1993.
Popovic, et al., "Gait Identification and Recognition Sensor," Proceedings of 6th Vienna International Workshop on Functional Electrostimulation, Sep. 1998, pp. 1-4.
Popovic, D., "Control of Movement for the Physically Disabled," Springer-Verlag London Limited, May 2000, pp. 270-302.
Popovic D., et al., "Control Aspects of Active Above-Knee Prosthesis," Int. Journal Man-Machine Studies, (1991) 35, pp. 751-767.
Popovic, M., "Angular Momentum Primitives for Human Walking: Biomechanics and Control," Proc. of the 2004 IEEE/RSJ International Conference on Intelligent Robots and Systems, Sep. 2004, Sendai, Japan., pp. 1685-1691.
Popovic, M., et. al., "Angular Momentum Regulation during human walking: Biomechanics and Control," Proceedings of the 2004 IEEE International Conference on Robotics and Automation, Apr. 2004, New Orleans, LA, pp. 2405-2411.
Popovic, M., et. al., "Zero spin angular momentum control: definition and applicability," Proceedings of the IEEE-RAS/RSJ International Conference on Humanoid Robots, Nov. 2004, Los Angeles, CA, pp. 1-16.
Popovic, M., et. al., "Ground Reference Points in Legged Locomotion: Definitions, Biological Trajectories and Control Implications," International Journal of Robotics Research, Dec. 2006, pp. 79-104.
Popovic, M. and Herr, H., "Global Motion Control and Support Base Planning," Proceedings of the IEEE/RSJ International Conference on Intelligent Robots and Systems, Aug. 2005, Alberta, Canada, pp. 1-8.
Popovic, M.B., W. Gu and H. Herr, "Conservation of Angular Momentum in Human Movement," MIT Al Laboratory-Research Abstracts, Sep. 2002. pp. 231-232, 2002.
Pratt, G. and Williamson M., "Series elastic actuators," Proceedings on IEEE/RSJ International Conference on Intelligent Robots and Systems, Jan. 1995, Pittsburgh, PA, pp. 399-406.
Pratt, G., "Legged Robots: What's New Since Raibert," IEEE Robotics and Automation Magazine, Research Perspectives, Sep. 2000, pp. 15-19.
Pratt, G., "Low Impedance Walking Robots," Integ. and Camp. Bioi., vol. 42, Feb. 2002, pp. 174-181.
Pratt, J., et. al., "The RoboKnee: An Exoskeleton for Enhancing Strength and Endurance During Walking", IEEE Conf. on Robotics and Automation, Apr. 2004, New Orleans, LA, pp. 2430-2435.
Prochazka, A. and Yakovenko, S., "The neuromechanical tuning hypothesis," Prog Brain Res, vol. 165, Oct. 2007, pp. 255-265.
Prochazka, A., et. al., "Positive force feedback control of muscles," J. of Neuro-phys., vol. 77, Jun. 1997, pp. 3226-3236.
Prochazka, A., et. al., "Sensory control of locomotion: reflexes versus higher-level control," Adv Exp Med Bioi, vol. 508, 2002, pp. 357-367.
Raibert, M., "Legged Robots that Balance," The MIT Press, Nov. 1986, Cambridge, MA, p. 89.
Rassier, D., et. al., "Length dependence of active force production in skeletal muscle," Journal of Applied Physiology, vol. 86, Issue 5, May 1999, pp. 1455-1457.
Riener, R., et. al., "Stair ascent and descent at different inclinations," Gait Posture, vol. 15, Feb. 2002, pp. 32-44.
Reitman, et. al., Gait analysis in prosthetics: opinions, ideas and conclusions, Prosthetics and Orthotics International, 2002, 26, 50-57.

(56) References Cited

OTHER PUBLICATIONS

Robinson, D., "Design and an analysis of series elasticity in closed-loop actuator force control," Ph.D. Thesis, MIT, Jun. 2000, Cambridge, MA, pp. 1-123.
Robinson, D., "Series elastic actuator development for a biomimetic walking robot," Proceedings of IEEE/ASME International Conference on Advanced Intelligent Mechatronics, Sep. 1999, pp. 561-568.
Rosen, J., et al., "A myosignal-based powered exoskeleton system," IEEE Transactions on Systems, Man, and Cybernetics-Part A: Systems and Humans, vol. 31, No. 3, May 2001, pp. 210-222.
Ruina, A., et. al., "A collisional model of the energetic cost of support work qualitatively explains leg sequencing in walking and galloping, pseudo-elastic leg behavior in running and the walk-to-run transition," Journal of Theoretical Biology, vol. 237, Issue 2, Jun. 2005, pp. 170-192.
Rybak, I., et. al., "Modelling spinal circuitry involved in locomotor pattern generation: insights from deletions during fictive locomotion," J Physiol, vol. 577 (Pt 2), Dec. 2001, 617-639.
Sanderson, D., et. al., "Lower extremity kinematic and kinetic adaptations in unilateral below-knee amputees during walking," Gait and Posture, vol. 6, No. 2, Oct. 1997, pp. 126-136.
Sanger, T., "Human arm movements described by a low-dimensional superposition of principal component," Journal of NeuroScience, vol. 20, No. 3, Feb. 2000, pp. 1066-1072.
Saranli, U., "RHex: A simple and highly mobile hexapod robot," Int. Jour. Rob. Res., vol. 20, No. 7, Jul. 2001, pp. 616-631.
Sarrigeorgidis K. and Kyriakopoulos K., "Motion control of the N.T.U.A. robotic snamek on a planar surface," Proc. of the 1998 IEEE International Conference on Robotics and Automation, May 1998, pp. 2977-2982.
Schaal, S., "Is imitation learning the route to humanoid robots?" Trends in Cognitive Sciences, vol. 3, Jun. 1999, pp. 233-242.
Schaal, S. and Atkeson, C., "Constructive incremental learning from only local information," Neural Computation, vol. 10, No. 8, Nov. 1998, pp. 2047-2084.
Scott, S. and Winter, D., "Biomechanical model of the human foot: kinematics and kinetics during the stance phase of walking," J. Biomech., vol. 26, No. 9, Sep. 1993, 1091-1104.
Sentis, L. and 0. Khatib, "Task-Oriented Control of Humanoid Robots Through Prioritization," IEEE-RAS/RSJ International Conference on Humanoid Robots, Nov. 2004, Santa Monica, CA, pp. 1-16.
Seyfarth, A., "Swing-leg retraction: a simple control model for stable running," J. Exp. Bioi., vol. 206, Aug. 2003, pp. 2547-2555.
Seyfarth, A., et. al., "A movement criterion for running," J. of Biomech., vol. 35, May 2002, pp. 649-655.
Seyfarth, A., et. al., "Stable operation of an elastic three-segmented leg," Bioi.Cybern., vol. 84, 2001, pp. 365-382.
Simon F., et. al, "Convergent force fields organized in the frog's spinal cord," Journal of NeuroScience, vol. 13, No. 2, Feb. 1993, pp. 467-491.
Sinkjaer, T., et. al., "Major role for sensory feedback in soleus Emg activity in the stance phase of walking in man," J Physiol, vol. 523, No. 3, Mar. 2000, pp. 817-827.
Skinner, H. and Effeney D., "Gait analysis in amputees," Am J Phys Med, vol. 64, Apr. 1985, pp. 82-89.
Smidt et al., "An Automated Accelerometry System for Gait Analysis," J. Biomechanics, vol. 10, 1977, pp. 367-375.
Srinivasan, M., "Energetics of legged locomotion: Why is total metabolic cost proportional to the cost of stance work," Proc. on ISB XXth Congress and the American Society of Biomechanics Annual Meeting, Jul. 2003, Cleveland, OH, pp. 829.
Stepien, J., et al., "Activity Levels Among Lower-Limb Amputees: Self-Report Versus Step Activity Monitor," Arch. Phys. Med. Rehabil., vol. 88, No. 7, Jul. 2007, pp. 896-900.
Sugano et al., "Force Control of the Robot Finger Joint equipped with Mechanical Compliance Adjuster," Proc. of the 1992 IEEE/RSJ Int. Conf. on Intel I. Robots & Sys., Jul. 1992, pp. 2005-2013.

Sugihara, T., et. al., "Realtime Humanoid Motion Generation through ZMP Manipulation based on Inverted Pendulum Control," Proceedings of the 2002 IEEE International Conference on Robotics and Automation, May 2002, Washington, DC, pp. 1404-1409.
Sup, F., "Design and Control of a Powered Transfemoral Prosthesis," The International Journal of Robotics Research, vol. 27, No. 2, Feb. 2008, pp. 263-273.
Taga, G., "A model of the neuro-musculo-skeletal system for human locomotion," Bioi. Cybern., vol. 73, No. 2, Jul. 1995, pp. 97-111.
Takayuki "Biped Locomotion using Multiple Link Virtual Inverted Pendulum Model," Publication of Electronics Information and Systems Society, vol. 120, No. 2, Feb. 2000, 8 pages.
Thorough man, K. and R. Shadmehr, "Learning of action through adaptive combination of motor primitives," Nature, vol. 407, Oct. 2000, pp. 742-747.
Tomovic R. et al., "A Finite State Approach to the Synthesis of Bioengineering Control Systems," IEEE Transactions on Human Factors in Electronics, vol. 7, No. 2, Jun. 1966, pp. 65-69.
Tong, et al., "A Practical Gait Analysis System Using Gyroscopes," Medical Engineering & Physics, vol. 21, Mar. 1999, pp. 87-94.
Turker, K., "Electromyography: some methodological problems and issues," Physical Therapy, vol. 73, No. 10, Oct. 1993, pp. 698-710.
van den Bogert, A., "Exotendons for assistance of human locomotion," Biomedical Engineering Online, Oct. 2003, pp. 1-8.
van den Bogert, et al. "A Method for Inverse Dynamic Analysis Using Accelerometry," Journal Biomechanics, vol. 29, No. 7, 1996, pp. 949-954.
Veltink P., et al., "The Feasibility of Posture and Movement Detection by Accelerometry," D-7803-1377-1/93, IEEE, Oct. 1993, pp. 1230-1231.
Vukobratovic M. and Juricic, D., "Contributions to the synthesis of biped gait," IEEE Transactions on Biomedical Engineering, vol. BME-16, No. 1, Jan. 1969, pp. 1-6.
Vukobratovic M. and Stepanenko J., "Mathematical models of general anthropomorphic systems," Mathematical Biosciences, vol. 17, Aug. 1973, pp. 191-242.
Walsh, C., "Biomimetic Design of an Under-Actuated Leg Exoskeleton for Load-Carrying Augmentation," Master's Thesis, MIT, Feb. 2006, pp. 1-94.
Waters, RL., "Energy cost of walking amputees: the influence of level of amputation," J Bone Joint Surg., vol. 58, No. 1, Jan. 1976, pp. 42-46.
Wilkenfeld, A., "An Auto-Adaptive External Knee Prosthesis," Artificial Intelligence Laboratory, MIT, Sep. 2000, Cambridge, MA, pp. 1-3.
Wilkenfeld, A. J., "Biologically inspired auto adaptive control of a knee prosthesis," Ph.D. Thesis, Massachusetts Institute of Technology, Oct. 23, 2000.
Williamson, M., "Series Elastic Actuators," Artificial Intelligence Laboratory, MIT, Jan. 1995, Cambridge, MA, pp. 1-74.
Willemsen A., et al., "Automatic Stance-Swing Phase Detection from Accelerometer Data for Peroneal Nerve Stimulation," IEEE Transactions on Human Factors in Electronics, vol. 37, No. 12, Dec. 1990, pp. 1201-1208.
Willemsen A., et al., "Real-Time Gait Assessment Utilizing a New Way of Accelerometry," Journal of Biomechanics, vol. 23, No. 8, 1990, pp. 859-863.
Williams, B., "Mode Estimation of Model-based Programs: Monitoring Systems with Complex Behavior," Proceedings of the International Joint Conference on Artificial Intelligence, Aug. 2001, Seattle, WA, pp. 1-7.
Winter, D. A, "Energy generation and absorption at the ankle and knee during fast, natural, and slow cadences," Clinical Orthopedics and Related Research, vol. 175, May 1983, pp. 147-154.
Winter, D, and Robertson D., "Joint torque and energy patterns in normal gait," Bioi. Cybem., vol. 29, May 1978, pp. 137-142.
Winter, D. and Sienko S., "Biomechanics of below-knee amputee gait," Journal of Biomechanics, vol. 21, No. 5, Aug. 1988, pp. 361-367.
Wisse, M., "Essentials of Dynamic Walking, Analysis and Design of two-legged robots," Ph.D Thesis, Technical University of Delft, 2004, pp. 1-195.

(56) References Cited

OTHER PUBLICATIONS

Woodward et al., "Skeletal Accelerations measured during different Exercises," Proceedings of the Institution of Mechanical Engineers, Part H: Journal of Engineering in Medicine, vol. 207, Jun. 1993, pp. 79-85.

Wu, The Study of Kinematic Transients in Locomotion Using the Integrated Kinematic Sensor, IEEE Transactions on Rehabilitation Engineering, vol. 4, No. 3, Sep. 1996, p. 193-200.

Yakovenko, S., et. al., "Contribution of stretch reflexes to locomotor control: a modeling study," Bioi Cybern, vol. 90, No. 2, Jan. 2004, pp. 146-155.

Yun X., "Dynamic state feedback control of constrained robot manipulators," Proc. of the 27th conference on Decision and Control, Dec. 1988, pp. 622-626.

Zlatnik, D., et. al., "Finite-state control of a trans-femoral prosthesis," IEEE Trans. on Control System Technology, vol. 10, No. 3, May 2002, pp. 408-420.

U.S. Appl. No. 13/347,443, Powered Joint Orthosis, filed Jan. 10, 2012.

U.S. Appl. No. 13/349,216, Controlling Powered Human Augmentation Devices, filed Jan. 12, 2012.

U.S. Appl. No. 13/417,949, Biomimetic Joint Acuators, filed Mar. 12, 2012.

\* cited by examiner

| GAIT CYCLE PHASE | PARAMETER | PARAMETER CHANGE FROM LEVEL-GROUND AT SELF-SELECTED WALKING SPEED (θ DEFINED POSITIVE IN FLEXION) | | | | | | | | |
|---|---|---|---|---|---|---|---|---|---|---|
| | | LEVEL GROUND | | | SLOPE/STAIR DESCENT | | | SLOPE/STAIR ASCENT | | |
| | | $\dot{s} < \dot{s}_{ss}$ | $\dot{s} \cong \dot{s}_{ss}$ | $\dot{s} > \dot{s}_{ss}$ | $\dot{s} < \dot{s}_{ss}$ | $\dot{s} \cong \dot{s}_{ss}$ | $\dot{s} > \dot{s}_{ss}$ | $\dot{s} < \dot{s}_{ss}$ | $\dot{s} \cong \dot{s}_{ss}$ | $\dot{s} > \dot{s}_{ss}$ |
| EARLY STANCE | $k_{es}$ | + | 0 | - | - | - | - | - | - | - |
| | $\theta_{es}$ | 0 | 0 | 0 | 0 | 0 | 0 | + | + | + |
| | $b_{es}$ | 0 | 0 | 0 | +- | + | ++ | - | - | +- |
| | $\Gamma_{es}$ | 0 | 0 | 0 | 0 | 0 | 0 | +- | + | ++ |
| LATE STANCE | $k_{ls}$ | 0 | 0 | 0 | 0 | 0 | 0 | 0 | 0 | 0 |
| | $\theta_{ls}$ | 0 | 0 | 0 | - | - | - | + | + | + |
| | $b_{ls}$ | 0 | 0 | 0 | + | + | + | - | - | - |
| | $P_{ff}$ | - | 0 | + | -+ | - | + | +- | + | ++ |
| | $N$ | - | 0 | - | + | + | ++ | +- | + | ++ |
| EARLY SWING | $\theta_{brake_{esw}}$ | + | 0 | + | - | - | - | - | - | 0 |
| | $\Gamma_{esw}$ | $\Gamma^* \cong \theta$ FOR BALLISTIC TRAJECTORY TO EXTENDED POSITION | | | | | | | | |
| LATE SWING | $k_{lsw}$ | 0 | 0 | 0 | - | - | - | - | - | - |
| | $\theta_{lsw}$ | 0 | 0 | 0 | + | + | 0 | + | + | + |
| | $b_{lsw}$ | + | 0 | - | - | - | +- | - | - | -+ |

FIG. 4C

TERRAIN ADAPTIVE POWERED JOINT ORTHOSIS

RELATED APPLICATIONS

This application claims priority to and benefit of U.S. Provisional Patent Application Ser. No. 61/435,045, filed on Jan. 21, 2011, the entire content of which is hereby incorporated by reference in its entirety.

FIELD OF THE INVENTION

This invention relates generally to powered human augmentation devices, such as lower-extremity prosthetic, orthotic, or exoskeleton apparatus, designed to emulate human biomechanics and to normalize function, components thereof, and methods for controlling the same.

BACKGROUND

Approximately 65% of service members seriously injured in Iraq and Afghanistan sustain injuries to their extremities. Many of these individuals experience muscle tissue loss and/or nerve injury, resulting in the loss of limb function or substantial reduction thereof. Many devices used for the treatment of lower-extremity pathology, e.g., knee orthoses, are passive devices. Increasingly, robotic technology is employed in the treatment of individuals suffering from limb pathology, either for the advancement of therapy tools or as permanent assistive devices. Upper-extremity robotic devices provide assistance and therapy for improved reaching and manipulation and, lower-extremity robotic devices have been developed for the enhancement of locomotor function.

Although decades of research has been conducted in the area of active permanent assistive devices for the treatment of lower-extremity pathology, these devices are not designed to produce a biomimetic response, generally described in terms of joint torque, joint angle, and other related parameters as observed in a human not having substantial muscle tissue injury and not using any device to assist in ambulation. Therefore, the robotic devices usually result in unnatural ambulation and may even cause significant discomfort to the wearer.

As such, many commercially available knee orthoses remain passive and non-adaptive to the wearer even today. These devices typically stabilize the knee joint medial-laterally, and limit the extent of knee flexion and extension. As such, they do not provide power or significant assistance to the user in walking, getting out of a chair, and ascending slopes and stairs, etc.

In level-ground walking, a healthy biological knee generally behaves like a spring during early to mid-stance, where knee torque is proportional to knee angular position. Further, during slope descent, the biological knee generally behaves like a variable damper, dissipating mechanical energy as heat to lower the body's center of mass with each step. Still further, during slope ascent, the biological knee behaves like a torque source, applying a non-conservative propulsive torque throughout early to mid-stance to lift the body's center of mass upwards with each step.

Some common major complications of knee extensor weakness are an inability to apply: 1) damping control during slope/stair descent, 2) spring stiffness control during early to mid-stance in level-ground walking, and 3) non-conservative propulsive torque control for slope/stair ascent and sit-to-stand maneuvers. Due to these various complications, a patient with knee extensor weakness frequently experiences a decrease in self-selected walking speed for level-ground and slope/stair ground surfaces, as well as an increase in walking metabolism while traversing these ground surfaces. Therefore, there is a need for improved systems and methods of permanent assistive devices for the treatment of lower-extremity pathology.

SUMMARY

In various embodiments, the present invention provides devices and methods for operating/controlling such devices so as to assist humans with knee extensor weakness, normalizing and/or enhancing the wearer's self-selected walking speed and metabolic economy. This is achieved using a type of device called Powered Knee Othosis (PKO); the PKO devices are capable of capable of spring stiffness control, dissipative damping control, and non-conservative torque control in both knee flexion and extension directions, in accordance with the gait-cycle, terrain (e.g., ground slope and stairs), and walking speed. As such, the PKO devices can adaptively provide a non-conservative propulsive torque to assist the user in walking, getting out of a chair, and ascending slopes and stairs.

The PKO devices can also augment knee torque during late stance, particularly during slope and/or stair ascent. Thus, the PKO devices can provide at least a biomimetic response and optionally can be used to enhance normal biomechanical response. Offering control enhancement for both stance and swing phases, a PKO device can be used as a permanent assistive device where actuation, sensing, power, and computation are all packaged within a small, lightweight, autonomous, manufacturable, and high cycle-life package that can readily fit within a normal pant leg, and can assist humans with weak or absent quadriceps. PKO devices can also assist humans having uninjured leg musculature in activities such as carrying a heavy load over a long distance and/or increasing elevation, to enhance their strength and endurance.

In one aspect, a method for assisting a person walking on a surface with a powered human augmentation device includes a controller. The method includes using the controller for determining a phase of a gait cycle, and estimating within the gait cycle, a slope of the surface. The method also includes supplying to a joint (e.g., knee) an augmentation torque, an impedance, or both. The impedance includes a linear spring component and a damping component. The method also includes modulating the augmentation torque and the impedance based on the phase of the gait cycle and the estimated slope, to provide at least a biomimetic response.

In some embodiments, the estimated slope is indicative of a walking mode such that level-ground walking mode corresponds to a substantially zero slope, downslope walking mode corresponds to a negative slope, and upslope walking mode corresponds to a positive slope. The downslope walking mode may include descending stairs and the upslope walking mode may include ascending stairs. The joint may be a knee.

In some embodiments, the method includes estimating walking speed, and the augmentation torque and/or the impedance may be based on the estimated walking speed. If the phase of the gait cycle is determined to be one of early stance and mid stance and the estimated slope is substantially zero, the impedance may be modulated such that contribution of the linear spring component to the modulated impedance is greater than contribution of the damping component. If the phase of the gait cycle is determined to be one of early stance and mid stance and the estimated slope is negative, however, the impedance is modulated such that contribution of the damping component is increased substantially compared to contribution thereof if slope is estimated to be substantially zero. Modulating the impedance may include varying the damping component according to the negative slope.

In some embodiments, the augmentation torque includes a non-conservative propulsive torque. If the phase of the gait cycle is determined to be one of early stance and mid stance and the estimated slope is positive, the non-conservative propulsive torque is provided such that the modulated augmentation torque is greater than the modulated augmentation torque applied if the slope is estimated to be substantially zero. If the phase of the gait cycle is determined to be late stance, the augmentation torque may be modulated to correspond to a reflex torque that is related to the estimated slope.

The method may include the step of modeling a joint equilibrium as a second-order response to a joint-position goal to be achieved prior to a next phase of the gait cycle. The modeling may be performed during a swing phase of the gait cycle. The method may also include determining if the joint is substantially fully flexed, during a swing phase of the gait cycle. If the joint is determined to be substantially fully flexed, modulating includes adjusting both the augmentation torque and the impedance to be substantially zero. In some embodiments, if the phase of the gait cycle is determined to be early swing, the augmentation torque is modulated according to the joint-equilibrium model such that a joint equilibrium corresponds to the joint-position goal. The impedance may be modulated according to the joint-equilibrium model such that a joint equilibrium corresponds to the joint-position goal.

In some embodiments, estimating the slope includes kinematically reconstructing a path of the joint (e.g., a knee) within the gait cycle. The method may also include kinematically reconstructing a path of another joint (e.g., an ankle) within the gait cycle, and associating the path of the other joint with the path of the joint to estimate the slope. The kinematic reconstruction may include computing a pose and an origin of a co-ordinate frame associated with a link connected to at least one of the joint and another joint proximal to the joint. The step of computing the pose may include creating a homogeneous transformation of the co-ordinate frame. In some embodiments, the homogeneous transformation includes a 3×1 vector defining an origin of the co-ordinate frame, and a 3×3 matrix comprising unit vectors of the co-ordinate frame. At least one point within the co-ordinate frame may correspond to a link connected to the joint and/or another joint proximal to the joint. The another joint may be an ankle joint and one point within the co-ordinate frame can be a distal end and/or a proximal end of a tibia connected to the ankle.

In some embodiments, the augmentation torque is modulated according to a positive-force feedback. The augmentation torque modulated according to the positive-force feedback, in combination with a natural joint torque supplied by the human, may approximate at least a normal joint torque. The positive-force feedback may include a gain and an exponent, and modulating may include adjusting the gain or the exponent, or both, according to the estimated slope and/or walking speed. The augmentation torque may be modulated according to a scaling factor and/or may be attenuated according to a protocol. The augmentation torque may be supplied in addition to natural joint torque supplied by the person to achieve at least a pre-determined total joint torque response.

In some embodiments, modulating includes applying a closed-loop torque control at the joint. To this end, the method may include modeling the joint torque, and determining the phase of the gait cycle based on the joint torque model. The augmentation torque, the impedance, and a joint equilibrium may be modulated in order to achieve at least a target walking speed, such as a walking speed desirable to the person. The augmentation torque, the impedance, and a joint equilibrium may also be modulated in order to substantially achieve a metabolic economy in accordance with a normative reference across at least one of walking speed and terrain.

In another aspect, embodiments of the invention feature a powered human augmentation device for assisting a person walking on a surface. The device includes a powered actuator for supplying to a joint an augmentation torque and/or an impedance that includes a linear spring component and a damping component. The device also includes a controller for (i) determining a phase of a gait cycle, (ii) estimating within the gait cycle a slope of the surface, and (iii) modulating the augmentation torque and the impedance based on the phase of the gait cycle and the estimated slope to provide at least a biomimetic response.

In some embodiments, the estimated slope is indicative of a walking mode, such that level-ground walking mode corresponds to a substantially zero slope, downslope walking mode corresponds to a negative slope, and upslope walking mode corresponds to a positive slope. The downslope walking mode may include descending stairs and the upslope walking mode may include ascending stairs. The joint may be a knee.

In some embodiments, the controller is adapted to estimate walking speed, and the augmentation torque, the impedance, or both may be based on the estimated walking speed. If the controller determines the phase of the gait cycle to be one of early stance and mid stance and the estimated slope is substantially zero, the powered actuator may be adapted to provide the modulated impedance such that contribution of the linear spring component to the modulated impedance is greater than contribution of the damping component. If the controller determines the phase of the gait cycle to be one of early stance and mid stance and the estimated slope is negative, the powered actuator may be adapted to provide the modulated impedance such that contribution of the damping component is increased substantially compared to contribution thereof if slope is estimated to be substantially zero. The controller may also be adapted to modulate the damping component according to the negative slope.

In some embodiments, the augmentation torque includes a non-conservative propulsive torque and, if the controller determines the phase of the gait cycle to be one of early stance and mid stance and the estimated slope is positive, the powered actuator may be adapted to provide the non-conservative propulsive torque such that the modulated augmentation torque is greater than the modulated augmentation torque applied if the slope is estimated to be substantially zero. If the controller determines the phase of the gait cycle to be late stance, the powered actuator may be adapted to provide the modulated augmentation torque, such that the modulated augmentation torque corresponds to a reflex torque that is related to the estimated slope.

In some embodiments, the controller is adapted to model, during a swing phase of the gait cycle, a joint equilibrium as a second-order response to a joint-position goal to be achieved prior to a next phase of the gait cycle. The device may include a joint angle sensor to provide a joint angle signal to the controller. If the controller determines, based on the joint angle signal, that the joint is substantially fully flexed, the powered actuator may adapted to adjust both the augmentation torque and the impedance to be substantially zero, during a swing phase of the gait cycle. If the controller determines the phase of the gait cycle to be early swing, the augmentation torque, impedance, or both may be modulated according to the joint-equilibrium model such that a joint equilibrium corresponds to the joint-position goal.

In some embodiments, the device includes an inertial measurement unit (IMU), and the controller may be adapted to kinematically reconstruct a path of the joint within the gait cycle based on a signal from the IMU. The controller may also be adapted to estimate the slope based on the kinematic reconstruction. The IMU may include an accelerometer and/or a gyroscope. The IMU may also include a first set of sensors associated with the joint (e.g., a knee) and a second set of sensors associated with another joint (e.g., an ankle). The controller may be adapted to kinematically reconstruct a path of the other joint within the gait cycle based on signals from the second set of sensors, and to associate the path of the other joint with the path of the joint to estimate the slope of the terrain.

The augmentation torque may be modulated according to a positive-force feedback. The augmentation torque modulated according to the positive-force feedback, in combination with a natural joint torque supplied by the human, may approximate at least a normal joint torque. The positive-force feedback may include a gain and an exponent, and modulating may include adjusting the gain, the exponent, or both according to the estimated slope and/or walking speed. The controller may be adapted to modulate the augmentation torque according to a scaling factor. In some embodiments, the device includes a communication interface for receiving a protocol, and the controller may be adapted to attenuate the augmentation torque according to the received protocol. The augmentation torque may be supplied in addition to natural joint torque supplied by the person to achieve at least a pre-determined total joint torque response.

In some embodiments, the controller is adapted to apply a closed-loop torque control at the joint. The controller may be adapted to model the joint torque, and to determine the phase of the gait cycle based on the joint torque model. The powered actuator may include a series-elastic actuator, and the series-elastic actuator may include a transverse-flux motor. In some embodiments, the series-elastic actuator includes a bilateral spring and a cable drive. The series-elastic actuator may also include a buckled beam and/or a unidirectional spring.

These and other objects, along with advantages and features of the embodiments of the present invention herein disclosed, will become more apparent through reference to the following description, the accompanying drawings, and the claims. Furthermore, it is to be understood that the features of the various embodiments described herein are not mutually exclusive and can exist in various combinations and permutations. As used herein, the term "substantially" means±10% and, in some embodiments, ±5%.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIG. 4c shows adjustment of various torque and impedance parameters according to terrain and/or walking speed, according to one embodiment;

DESCRIPTION

The entire contents of each of U.S. patent application Ser. No. 12/157,727 "Powered Ankle-Foot Prosthesis" filed on Jun. 12, 2008 (Publication No. US2011/0257764 A1); U.S. patent application Ser. No. 12/552,013 "Hybrid Terrain-Adaptive Lower-Extremity Systems" filed on Sep. 1, 2009 (Publication No. US2010/0179668 A1); U.S. patent application Ser. No. 13/079,564 "Controlling Power in a Prosthesis or Orthosis Based on Predicted Walking Speed or Surrogate for Same" filed on Apr. 4, 2011; and U.S. patent application Ser. No. 13/079,571 "Controlling Torque in a Prosthesis or Orthosis Based on a Deflection of Series Elastic Element" filed on Apr. 4, 2011 are incorporated herein by reference.

Figure 1:
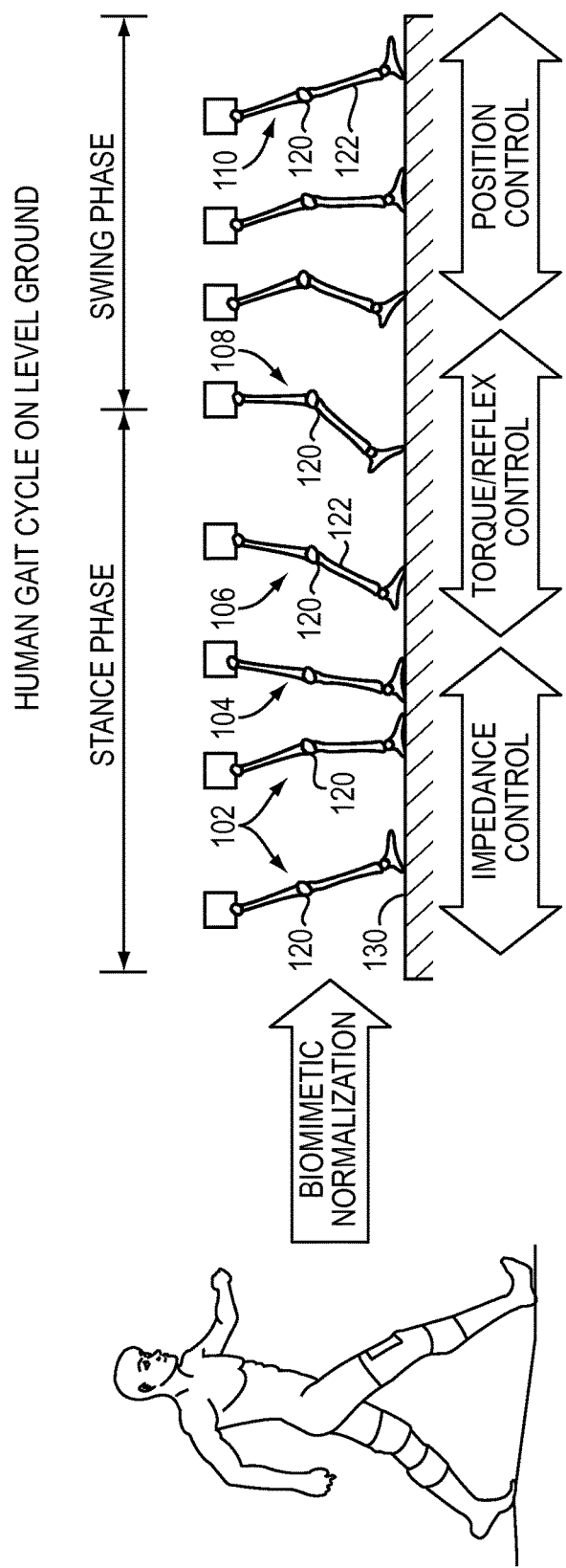
FIG. 1 illustrates biological knee function of an average human in the stance and swing phases of a human gait cycle during level-ground ambulation.

FIG. 1 illustrates biological knee function in the stance and swing phases of a human gait cycle during level-ground ambulation. Throughout early stance 102 to mid stance 104 the knee 120 typically responds as a linear spring. This form of mechanical impedance (which can take the form of a spring, inertia or damper, acting alone or in combination) serves to cushion the foot-strike impact in accordance with the gait speed. In late-stance 106, the knee 120 generally behaves as a torque source in the form of a reflex to lift the lower leg 122 off the ground surface 130 during initiation portion 108 of the swing phase. The reflex release may arise from a positive force feedback mechanism within the gastrocnemius muscle. In the terminal portion 110 of the swing phase, the knee 120 first brakes the swinging lower leg 122 to limit heel rise after toe-off and then positions the lower leg 122 optimally for absorbing energy prior to foot strike initiation in the next gait cycle.

Figure 2:
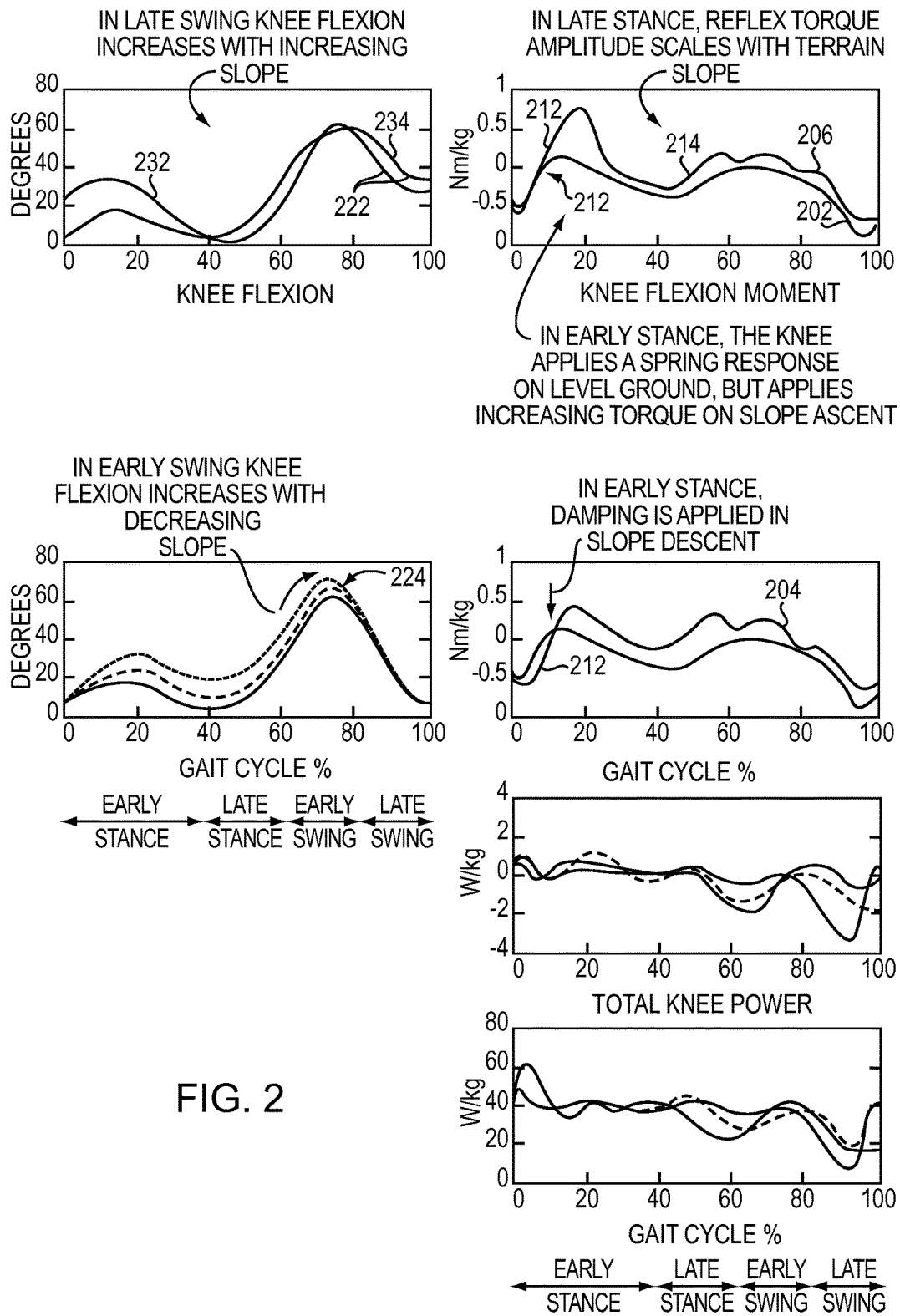
FIG. 2 illustrates how the knee response of an average human, described in terms of angle, moment (i.e., torque), and power, changes as a function of terrain slope.

Typically, the human gait adapts to terrain modality, e.g., ground slope and whether the human is ascending or descending stairs, and to walking speed so as to maintain balance and to achieve a metabolically economical movement pattern. FIG. 2 illustrates how the knee response, described in terms of angle, moment (torque), and power, changes as a function of terrain slope. For example, during level-ground walking depicted by curve 202, the biological knee behaves like a spring, where knee torque is proportional to knee angular position, during early to mid-stance 212. During slope descent, depicted by curve 204, the biological knee behaves like a variable damper, dissipating mechanical energy as heat to lower the body's center of mass with each step, during early to mid-stance 212. The variable damping generally increases as the declination angle increases. Such behavior may also be invoked during stair descent. During slope ascent, depicted by curve 206, the biological knee behaves like a torque source, applying a non-conservative propulsive torque throughout early to mid-stance 212 to lift the body's center of mass upwards with each step. Such behavior is usually also invoked upon stair ascent. A slope-dependent reflex is applied in late stance 214.

Flexion angle in the swing phase also shows terrain dependence. In slope ascent, the flexion angle just prior to foot-strike, i.e., late swing 222 of the curve 232 increases with the slope of ascent, whereas the knee flexion is invariant with the slope of descent, as depicted by the curve 234. To achieve sufficient toe clearance on descent, the knee flexion angle increases in early swing 224 as the descent becomes steeper. Though the data presented in FIG. 2 are captured at a substantially constant gait speed, it is understood that the above impedance and torque response on level ground and slopes typically changes with gait speed, in part, to account for changes in the body momentum and to deliver/absorb power accordingly.

PKO platforms 500, 800 described with reference to FIGS. 5 and 8, respectively, can discriminate terrain modality and speed within a gait cycle (intra-cycle), and can also adapt the impedance, reflex, and position response in accordance with that terrain and gait speed. Intra-cycle sensing is advantageous, because during an average walk terrain and walking speed may change frequently. The platforms 500, 800 employ a six-degree-of-freedom inertial measurement unit (IMU) capable of computing the path of the ankle joint and the distal-end of the femur (knee), from which the IMU can discriminate and discern terrain modality, including stairs and slopes, as illustrated with reference to FIG. 11b. The path of the hip can be used to augment the information from the knee and ankle. For instance, in stair ascent, the hip is generally stationary as the knee flexes, a precursor that is not evident when a wearer is traversing sloping and/or level ground.

Figure 3A:
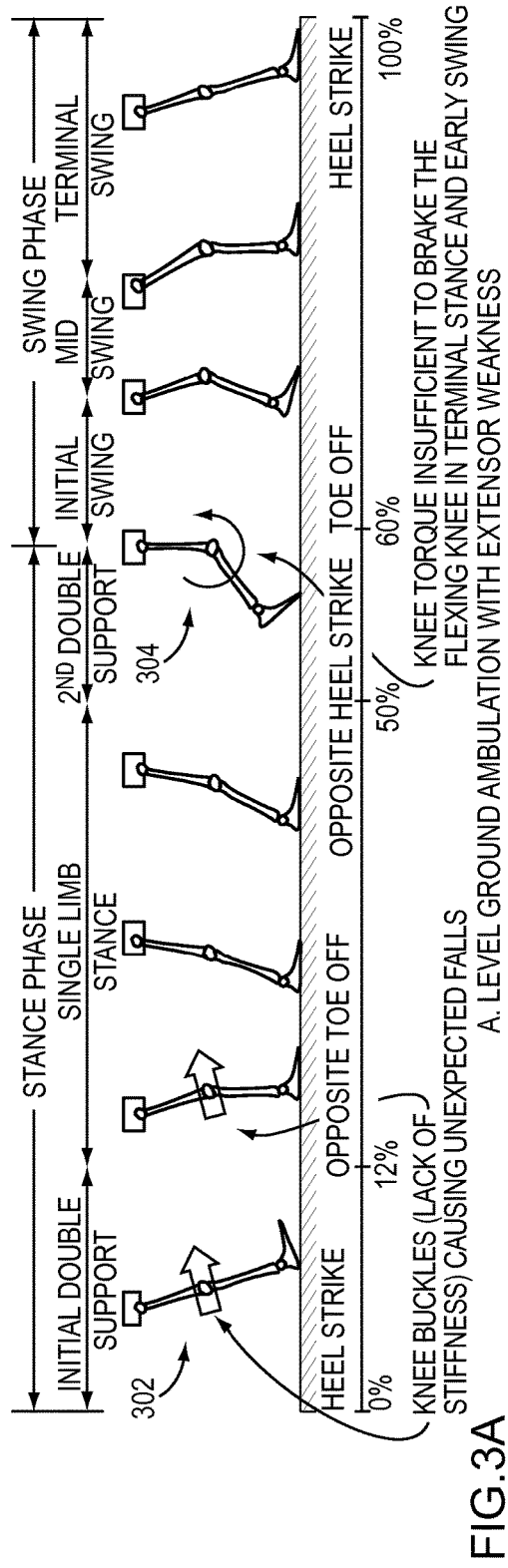
FIG. 3a illustrates how the knee response may become impaired when the quadriceps extensors are weakened.

FIG. 3a illustrates how the knee response may become impaired when the quadriceps extensors are weakened. In early stance 302, the knee stiffness can be insufficient to absorb energy either as a spring as in level-ground ambulation or as a damper in steep descent. In late stance 304, the knee torque is insufficient to "brake" the knee and to deliver sufficient reflex particularly in steep ascent and descent.

Figure 3B:
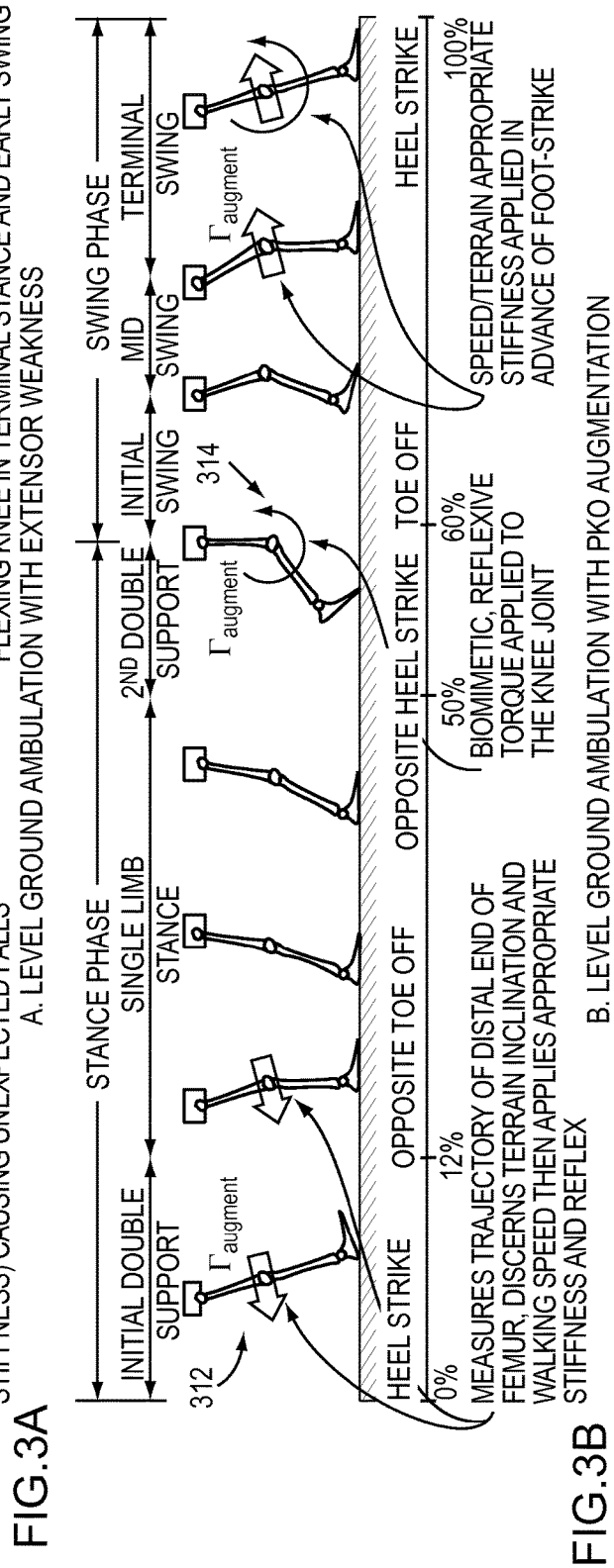
FIG. 3b illustrates how the knee response of FIG. 3a can be augmented, according to one embodiment.

When worn by a wearer with weakened quadriceps extensors, the PKO platforms 500, 800 deliver an augmentation torque, $\Gamma_{augment}$, to normalize the response, i.e., to produce a response that may be produced by a joint (e.g., knee) of average humans not having weakened muscle tissue (e.g., quadriceps extensors) and not wearing any powered prosthetic/orthotic devices. With reference to FIG. 3b, just prior to foot-strike in early stance 312, the PKO platforms 500, 800 apply a computed knee flexion angle and set the impedance, for energy absorption, in accordance with terrain slope. The terrain slope can be inferred from the ankle and knee trajectories and with instantaneous gait speed inferred from the IMU-computed angular pitch rate of the femur and tibia.

Once the foot strikes the ground in early stance 312, the PKO platforms 500, 800 apply appropriate knee extensor torque, $\tau_{extensor}$, to achieve an impedance relation of the form:

$$\tau_{extensor} = \Gamma_0(\phi, \dot{s}) - k_{\phi,\dot{s}}(\theta - \theta_0) - b_{\phi,\dot{s}}\dot{\theta}$$

in accordance with the computed terrain slope and speed. In late stance 314, the PKO platforms 500, 800 apply additional torque and reflex in accordance with the terrain slope and the instantaneous gait speed inferred by femur and tibia pitch rates. In late stance 314, the knee extensor torque corresponds to a biologically-conceived, non-linear, positive torque feedback relation of the form:

$$\tau_{extensor} = P_{f_{\phi,\dot{s}}} \left(\frac{\Gamma_{knee}}{\Gamma_0}\right)^{N_{\phi,\dot{s}}}$$

where the gain, $P_{f_{\phi,\dot{s}}}$ is a function of terrain slope, $\phi$, and gait speed, and the exponent, $N_{\phi,\dot{s}}$, is also a function of terrain slope and gait speed. $\Gamma_{knee}$ is an intrinsic measure of knee torque in the above relation that includes the contribution of both the "locking torque" of the knee and the normalized extensor/flexor contribution. In general, both the gain and the exponent are increased to achieve the higher reflex torques needed as the slope of ascent and descent increase.

Figure 4A:
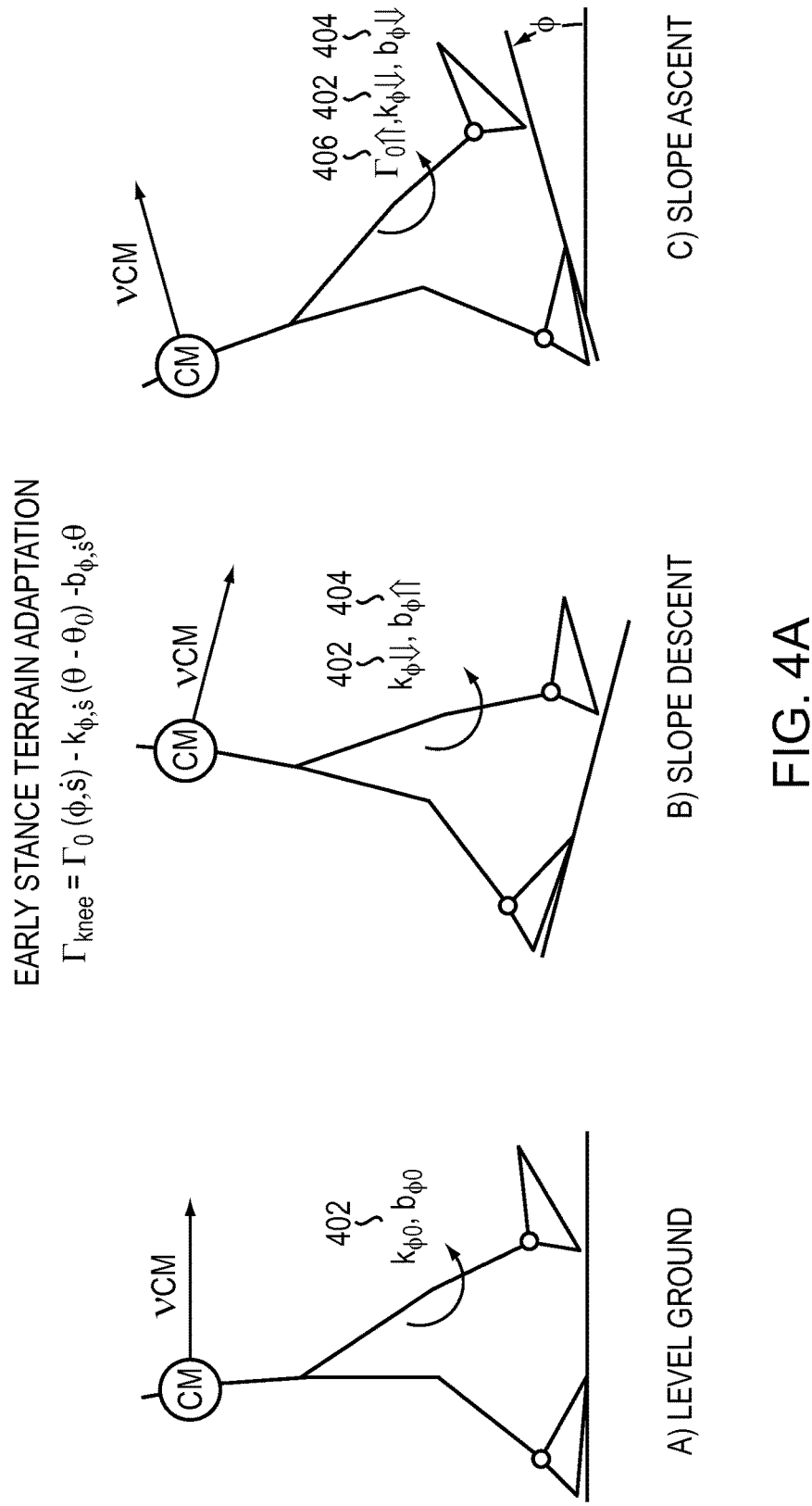
FIGS. 4a and 4b schematically illustrate, during early stance and late stance, respectively, the terrain-based modulation of various components of knee extensor torque supplied by a powered augmentation device so as to normalize the knee response, according to one embodiment.

With reference to FIG. 4a, in early stance, during level-ground walking, the linear spring component k 402 of the extensor torque applied by the PKO platforms 500, 800 is significant. While descending slope, the linear spring component k 402 is decreased and the damping component b 404 is increased, such that the damping component b 404 is significant. While ascending slope, both the linear spring k 402 and damping component b 404 are decreased and a non-conservative propulsive torque component $\Gamma_0$ 406 is increased.

Figure 4B:
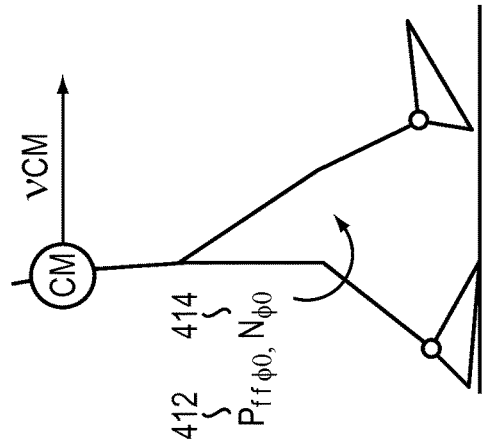

With reference to FIG. 4b, in late stance, during level-ground walking, the knee extensor torque applied by the PKO platforms 500, 800 corresponds to non-linear, positive torque feedback determined by gain 412 and exponent 414. While descending slope, the gain 412 is decreased and the exponent 414 is increased. While ascending slope, both the gain 412 and exponent 414 are increased. Adjustment of various torque and impedance parameters according to terrain and/or walking speed is described in a Table in FIG. 4c. Thus, the PKO platforms 500, 800 can emulate human knee behavior during the gait cycle by biomimetically applying impedance, torque, and joint equilibrium control in accordance with the gait cycle and speed, and augment the knee torque of the wearer to provide at least a normalized knee response.

Figure 5:
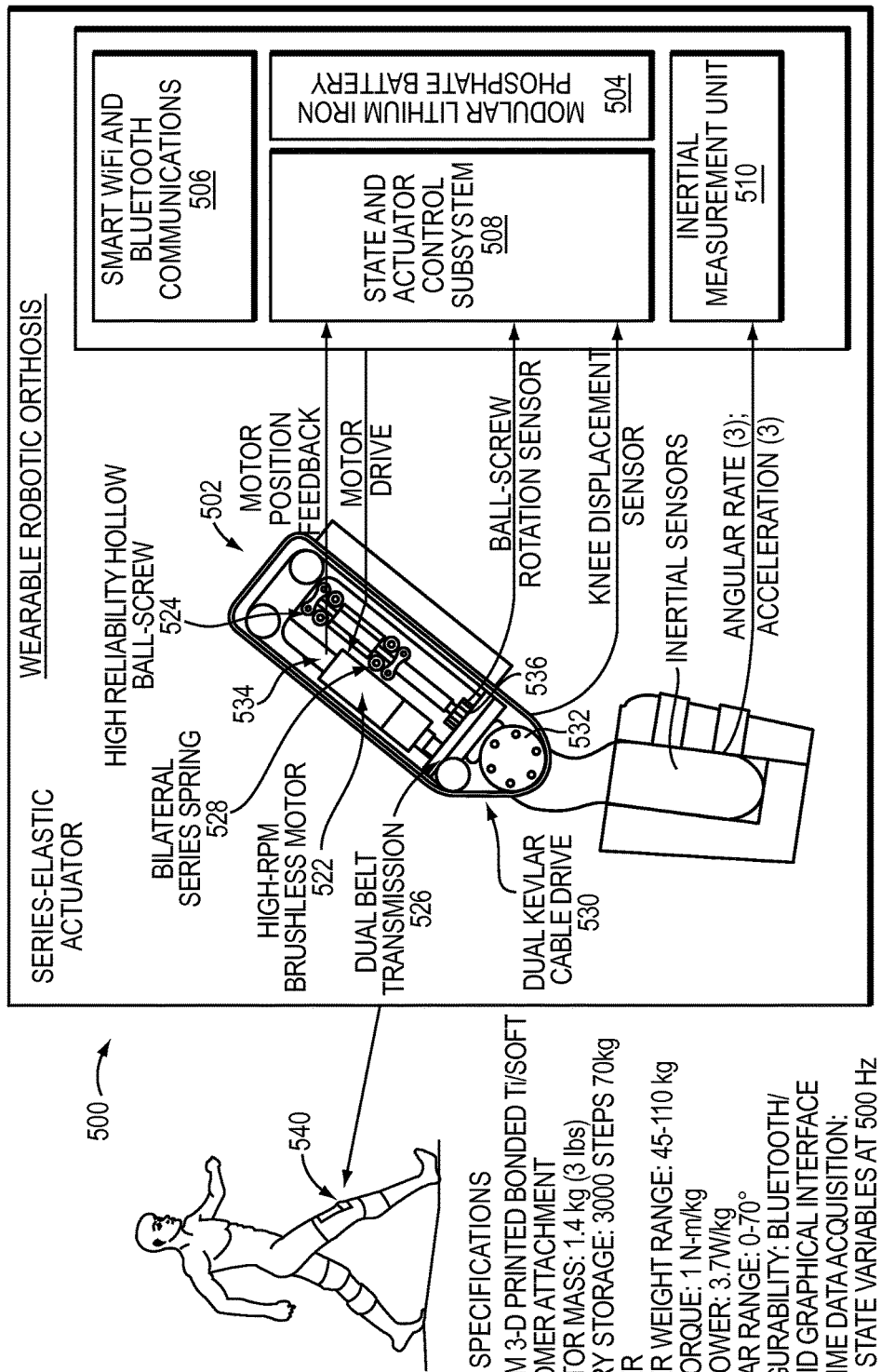
FIG. 5 schematically depicts a powered augmentation device according to one embodiment.

With reference to FIG. 5, the PKO platform 500 uses a quiet, light-weight, and rugged actuator 502. A modular battery 504 having a 3000 step capacity (typically for a wearer weighing about 70 kg with significant quadriceps extensor weakness) is used. A typical wearer may need to replace this lightweight battery pack 504 between one and two times per day. The actuator 502 can deliver at least biomimetic torque and angle response within a gait speed range from about 0 up to about 1.75 m/sec.

Optionally, the Platform 500 may employ one or two embedded wireless interfaces 506. A Bluetooth® interface may be used as the pathway for PDA-based tuning by clinicians and researchers to normalize the torque response, e.g., by specifically programming the PKO platform 500 to deliver augmentation torque $\Gamma_{augment}$ as required in each phase of the gait cycle as described below with reference to FIG. 7. A smart WiFi interface may serve as the pathway for researchers to acquire control state variables and sensory feedback from the PKO platform 500 and to synchronize this telemetry with external biomechanical instrumentation.

The actuator 502 of the PKO platform 500 can be a series-elastic actuator (SEA) to drive the powered orthosis. See, for example, U.S. Pat. No. 5,650,704 "Elastic Actuator for Precise Force Control" the disclosure of which is incorporated herein by reference. A multi-processor control system (State and Actuator Controller) 508 uses feedback from the SEA to deliver the appropriate response in accordance with the phase of the gait cycle, the terrain, and the walking speed. A three-phase brushless motor driver (Motor Driver) 522 interfaces to the State and Actuator Controller 508 to accomplish closed-loop torque control of the SEA 502. An Inertial Measurement Unit (IMU) 510, employing a three-axis rate gyro and a three-axis accelerometer, provides feedback to sense transitions between phases of the gait cycle, to measure gait speed, and to discriminate terrain modality. The WiFi/Bluetooth® communication module 506 is employed to interface directly to the State Controller and Actuator Controller 508 to facilitate data acquisition and PDA-based clinician tuning.

The SEA 502 may employ a robust ball-screw mechanism 524 driven by the high-rpm brushless motor 522 through a redundant aramid fiber twin belt transmission 526. The ball-nut 524 of the SEA 502 drives the knee 540 through a bilateral spring assembly 528 and a redundant aramid fiber cable drive 530. The bilateral spring assembly 528 can exhibit a weak stiffness in flexion and a stiffer spring in extension as would be applied in locking the knee joint. Thus in this embodiment, the bilateral spring 528 is used (i) to store energy in late stance for later release in the reflex response and (ii) to serve as a sensing means for achieving closed-loop torque control of the actuator 502. By storing energy for later release, the peak power and, hence, size and weight of the motor 522 are reduced by over 40% compared to an actuator without the spring storage, in this embodiment. Displacement of the spring 528 can be used to estimate and thereby control drive torque in a way that attenuates the effect of friction, enabling a backdrivable means of actuation that replicates biological knee operation.

A knee sensor 532, a motor-position sensor 534, and a ball-screw position sensor 536 embedded in the actuator 502 are employed to determine a state of the actuator 502 and to provide a basis for brushless motor control and for modulation of impedance, torque, and position in accordance with the phase of the gait cycle and gait speed. To this end, the State Controller and Actuator Controller 508 implements a state machine.

Figure 6:
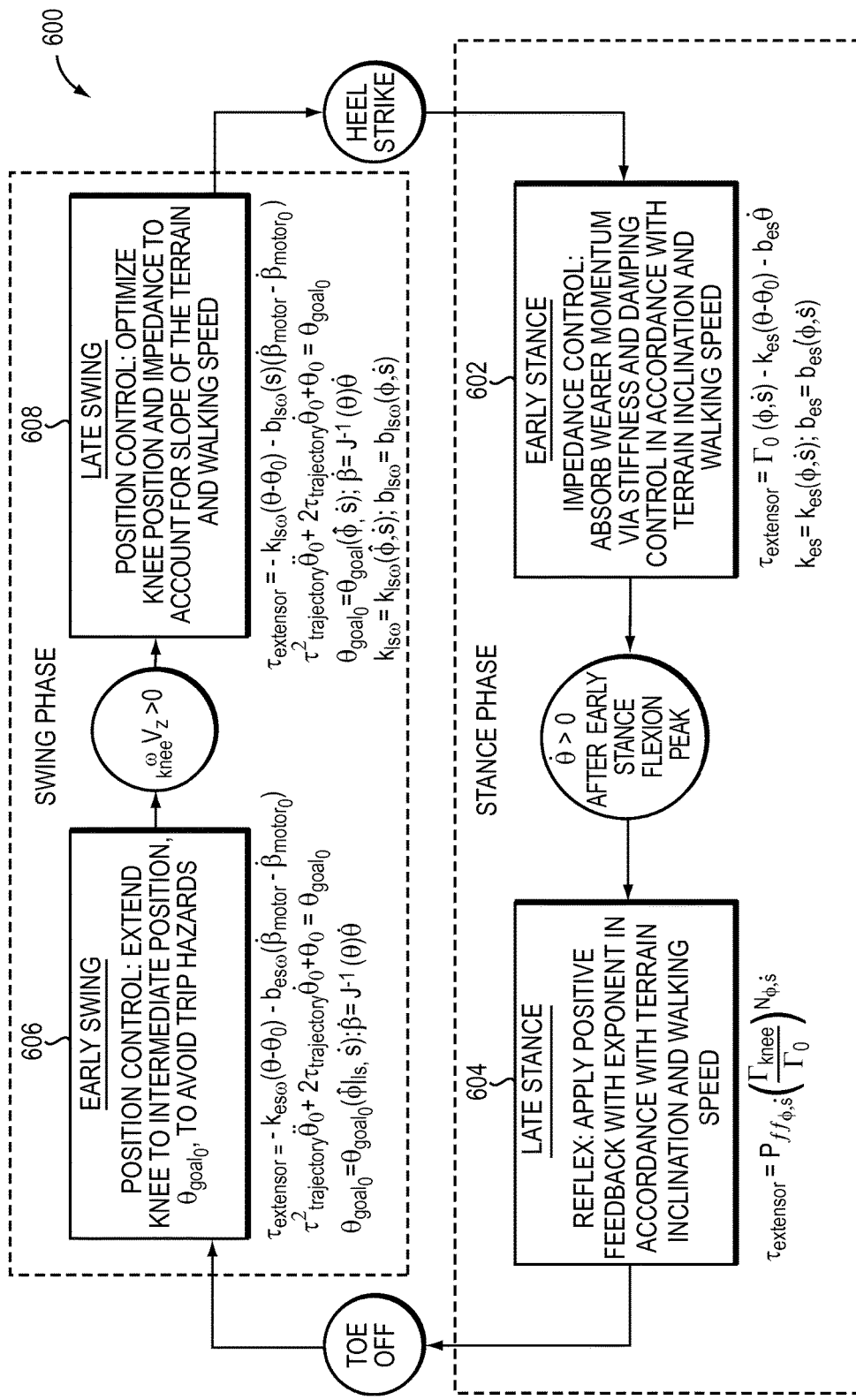
FIG. 6 illustrates the operation of a state machine of a powered augmentation device according to one embodiment.

With reference to FIG. 6, during early stance state 602, the state machine 600 adapts the PKO platform 500 to apply a linear spring and damping impedance in accordance with the gait speed and terrain angle, given by:

$$\tau_{extensor} = \Gamma_0(\phi, \dot{s}) - k_{\phi, \dot{s}}(\theta - \theta_0) - b_{\phi, \dot{s}}\dot{\theta}$$

$$k_{cp} = k_{cp}(\phi, \dot{s}); b_{cp} = b_{cp}(\phi, \dot{s})$$

Where
$\tau_{extensor}$ is the commanded SEA motor torque
$\theta$ is the ankle angle,
$\phi$ is the terrain angle, and
$\dot{s}$ is the estimated gait speed at foot-strike estimated by the IMU Transition into the early stance state 602 is accomplished by sensing by the IMU 510 the distinctive vibration that occurs when the foot strikes the ground. The impedance is configured and scaled so as to prevent buckling of the knee in accordance with walking speed and the response needed to at least normalize the augmented response of the wearer.

Transition into the late stance state 604 generally occurs when the detected knee extension angle velocity changes from negative to positive. In this state 604, a reflex response can be achieved through non-linear positive feedback as described by the relation:

$$\tau_{extensor} = P_{ff_{\phi,\dot{s}}} \left( \frac{\Gamma_{knee}}{\Gamma_0} \right)^{N_{\phi,\dot{s}}}$$

In this, the reflex gain, $P_{ff}(\phi,\dot{s})$ and the exponent (non-linear spring), $N(\phi,\dot{s})$ are each a function of the terrain angle, $\phi$, and the estimated gait speed, $\dot{s} = \dot{s}(\dot{\psi}_{femur}, \dot{\psi}_{tibia})$, which is a function of the instantaneous angular rate of the tibia and femur at the time of entry in to the late stance state 604. A hard stop spring model for extreme knee extension, $\Gamma_{knee}(\theta)$, is used to model the wearer torque response at extremes of extension ($\theta > 0$) while the knee is locked so that at least a biomimetic response is achieved.

Transition into early swing state 606 occurs when the detected SEA 502 torque, $\Gamma_{SEA}$, approaches a programmable percentage of peak torque. In this state 606, position control is employed to brake the knee flexion velocity, to achieve proper ground clearance and heel rise during the early to mid swing phase through use of an organically-derived trajectory, $\theta_0(t)$ that smoothly decelerates to a goal position in a nearly ballistic trajectory (i.e., small torque corresponding to a lightly damped pendulum), $\theta_{goal} = \theta_{goal_0} = \theta_{goal_0}(\hat{\phi}|_{ls}, \dot{s})$:

$$\tau_{extensor} = -k_{esw}(\theta - \theta_0) - b_{esw}(\dot{\beta}_{motor} - \dot{\beta}_{motor_0})$$

$$\tau_{trajectory}^2 \ddot{\theta}_0 + 2\tau_{trajectory}\dot{\theta}_0 + \theta_0 = \theta_{goal_0}$$

$$\theta_{goal_0} = \theta_{goal_0}(\hat{\phi}|_{ls}, \dot{s}); \dot{\beta} = J^{-1}(\theta)\dot{\theta}$$

where $\beta_{motor}$ is the motor angle corresponding to a knee angle with zero SEA spring displacement. and
$\hat{\phi}|_{ls}$ is estimated terrain angle as estimated at the end of late stance using the inertial tibia and femur angular velocities.

Also in the early swing state 606, the inertial ankle and knee trajectories are computed and used to discriminate between the three modalities, i.e., slope/stair ascent, slope/stair descent, and walking on substantially level ground. This early discrimination may be used to adjust the control parameters of the State Controller and Actuator Controller 508 in advance of foot strike to achieve seamless response across the swing-stance transition.

Transition into late swing state 608 occurs when the IMU 510 detects a negative, vertical Cartesian (world-frame referenced) ankle pivot velocity, $^{W}V_{ankle\ pivot_z}$. In this state 608, position control is used with a smooth trajectory that converges to a time-varying goal point, $\theta_{goal}$, that is a function of gait speed and terrain slope, each estimated by the IMU 510 which in some embodiments uses only intra-gait-cycle information. The impedance (stiffness and damping) applied to position and velocity errors referenced to the trajectory (equilibrium), $\theta_0(t)$ may be preferably set in accordance with gait speed and terrain angle.

Figure 7:
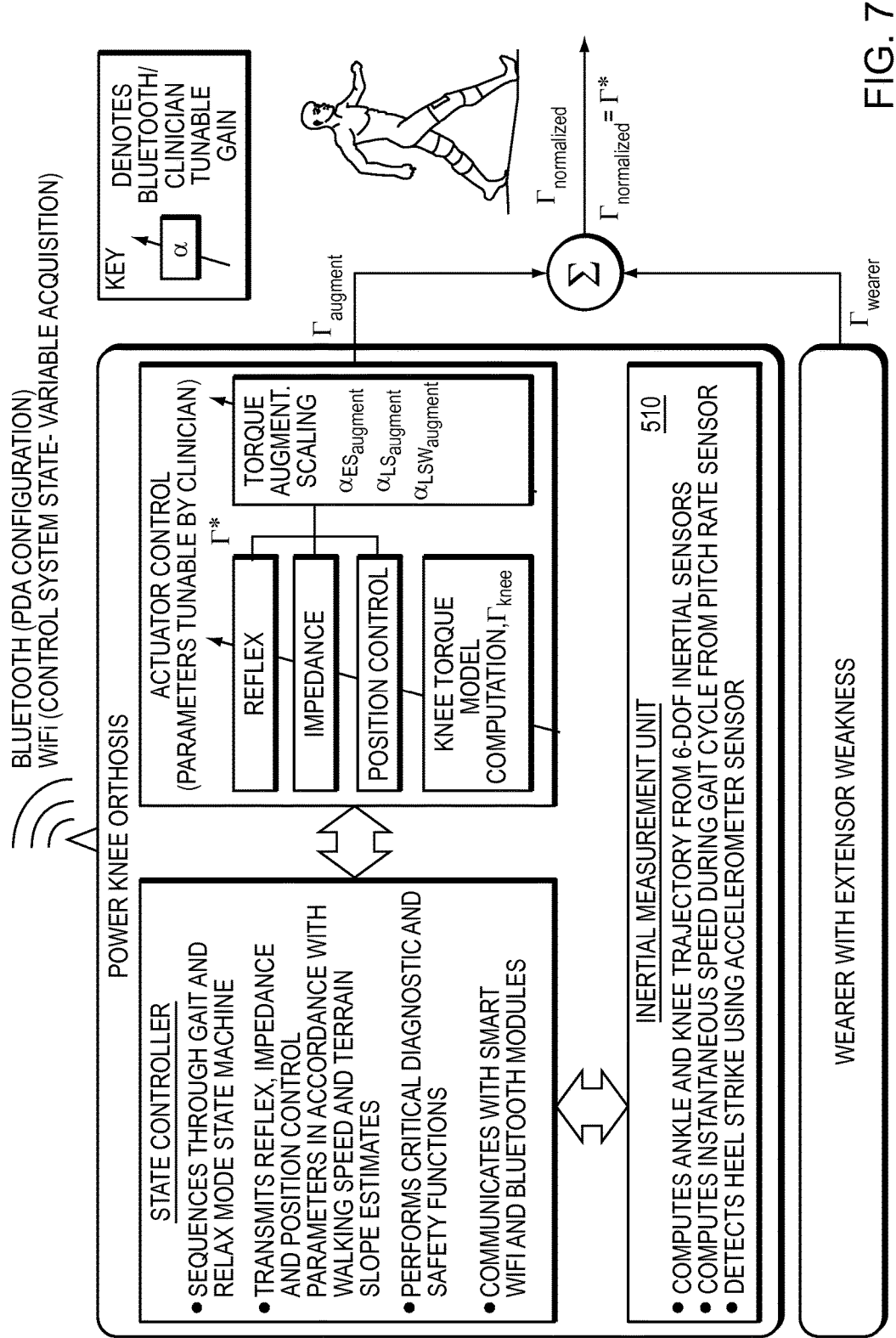
FIG. 7 illustrates the operation of a powered augmentation device implementing the state machine of FIG. 6, according to one embodiment.

FIG. 7 illustrates how the PKO platform 500 can augment the torque of a wearer to achieve at least a normalized biomimetic response. In some embodiments, a powered augmentation device can augment the torque and adjust impedance to achieve a response that can enable a wearer who does not have a diminished natural joint function to perform activities such as walking or running a long distance, carrying a heavy load, climbing steep slopes, etc. The state machine 600 modulates the SEA 502 impedance, reflex, and position control response in accordance with gait speed and terrain modality inputs from the IMU 510. The SEA 502 control internally computes at least the normalized biomimetic torque, $\Gamma^*$, in each state of the gait cycle. State-specific attenuation, set by the clinician, then scales $\Gamma^*$ and drives the SEA 502 to deliver just the right torque, $\Gamma_{augment}$, to add to the wearer's natural torque response, $\Gamma_{wearer}$, to approximate $\Gamma^*$, i.e., the desired normalized biomimetic response or an enhanced response that may allow a person to undertake activities such as walking fast (e.g., 2 m/sec.) for a long time e.g., about 6 hours.

Battery conservation is important in wearable PKO devices. In the absence of battery energy, or when the walking state machine (e.g., the state machine 600, illustrated with reference to FIG. 6) detects that the wearer has stopped walking (which can be determined by absence of gait-cycle phase transition for over approximately two seconds), the control system shorts the motor leads to ground using power electronics. In this special damping mode the motor leads are shorted together, creating a dynamic brake with damping torque, $$\tau_{motor} = -b_{sl}\omega = -\frac{(k_g k_t)^2}{R}\omega,$$

where $b_{sl}$ is the shorted leads damping, $k_g$ is the gear ratio between the motor and joint output, $k_t$ is the motor constant in Nm/A and R is the motor resistance, and $\omega$ is the rotation rate of the joint. In the "shorted leads" operation, the time constant, $\tau^{sl}$, that describes the first-order spring-damper actuator dynamics comprising the series-spring, $k_{SEA}$ and the intrinsic actuator damping, $b_{sl}$, is given by the relation, $$\tau_{sl} = \frac{b_{sl}}{k_{SEA}},$$

In transverse-flux and other high-torque motor actuators, the $\tau_{sl}$ may be on the order of about 500 msec or more. For time intervals, e.g., less than ⅓ of the time constant, the actuator 502 in "shorted leads" mimics a static clutch, taking no energy from the battery. By matching the series-stiffness with that required in early stance flexion, the motor clutch is engaged at the desired joint equilibrium so as to approximate the biomimetic linear spring response without requiring any battery energy. This affords significant advantage in system design, response, and economy of operation.

Figure 8A:
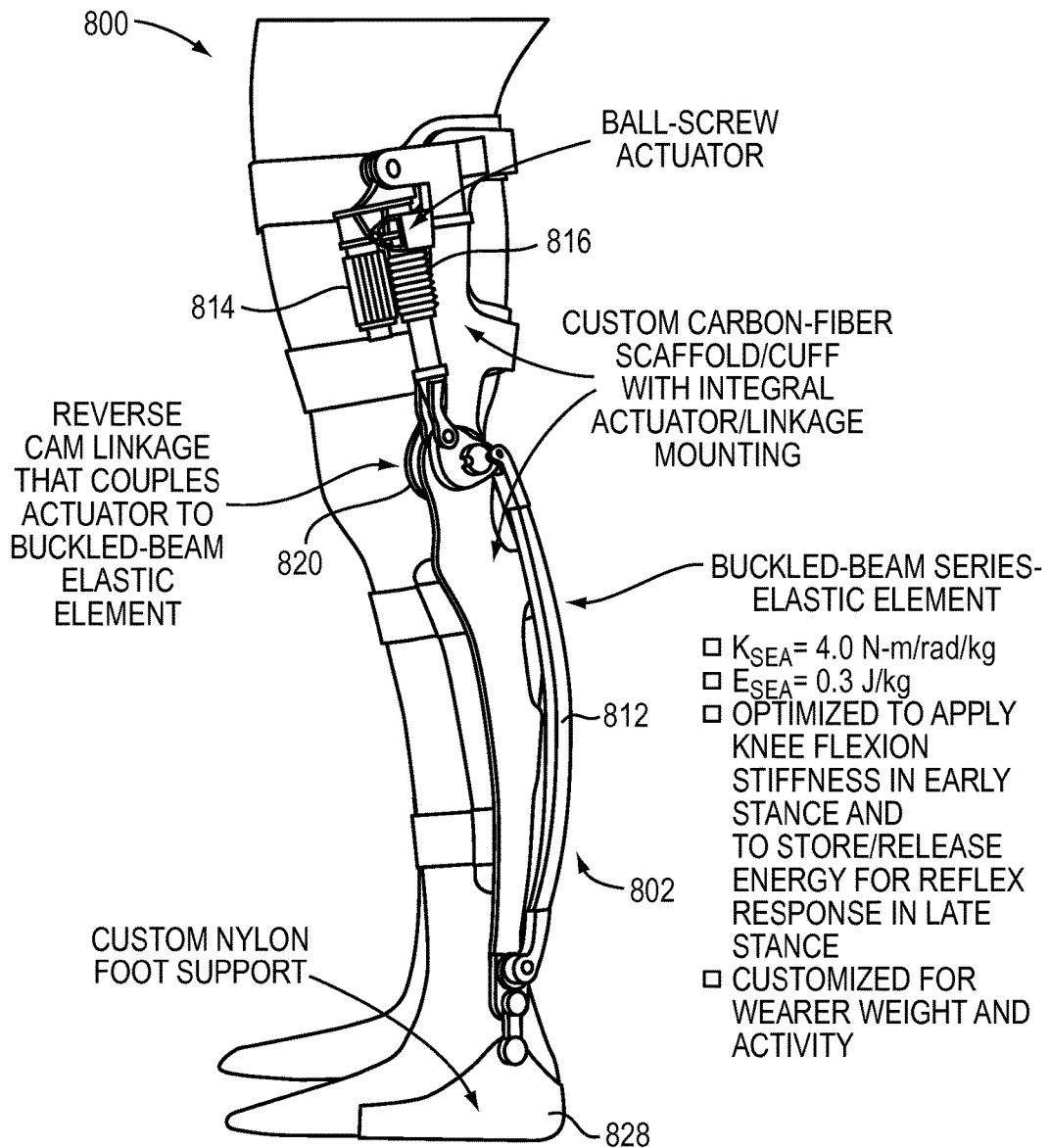
FIGS. 8a-8c schematically depict a powered augmentation device according to another embodiment.
Figure 8B:
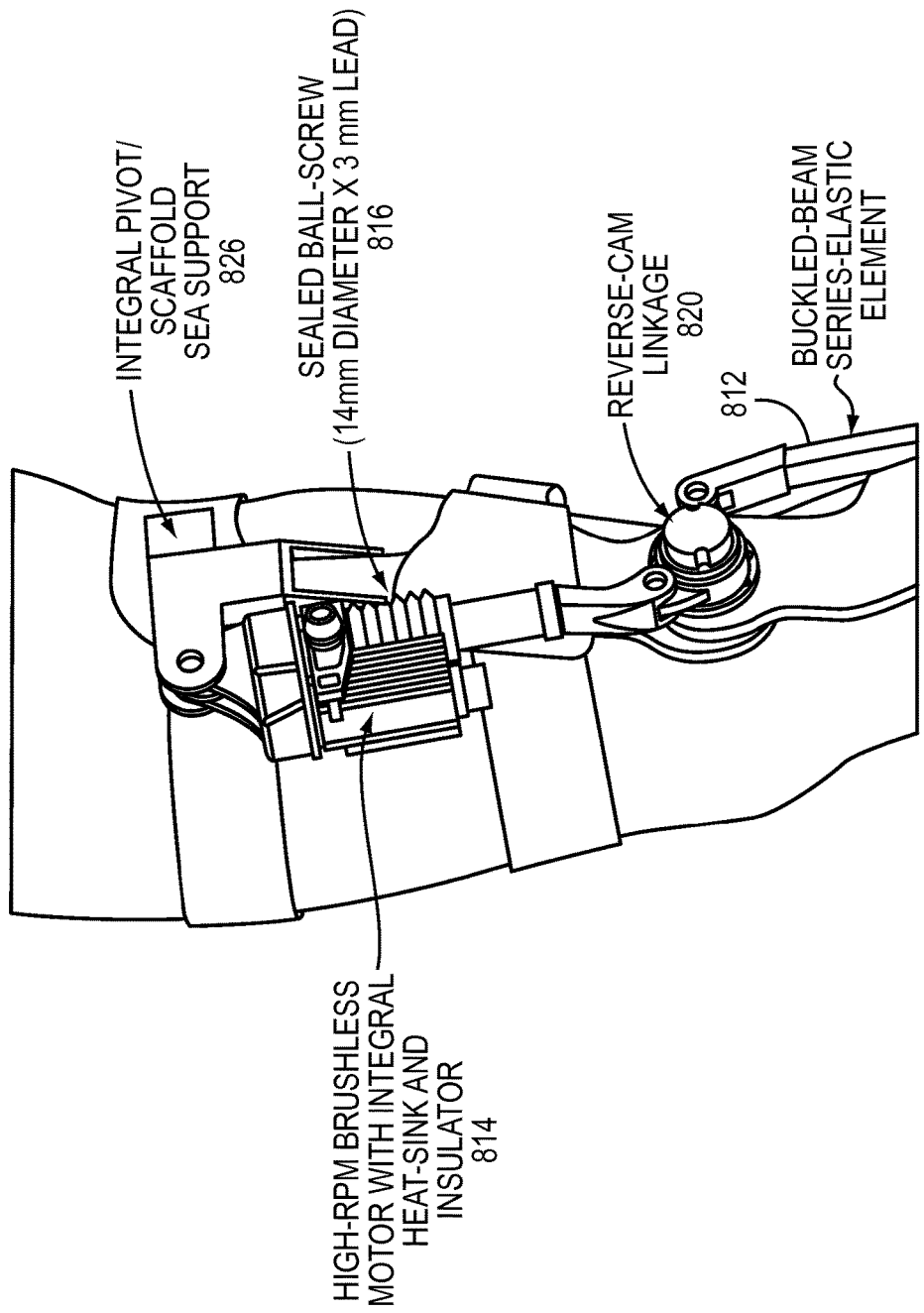
Figure 8C:
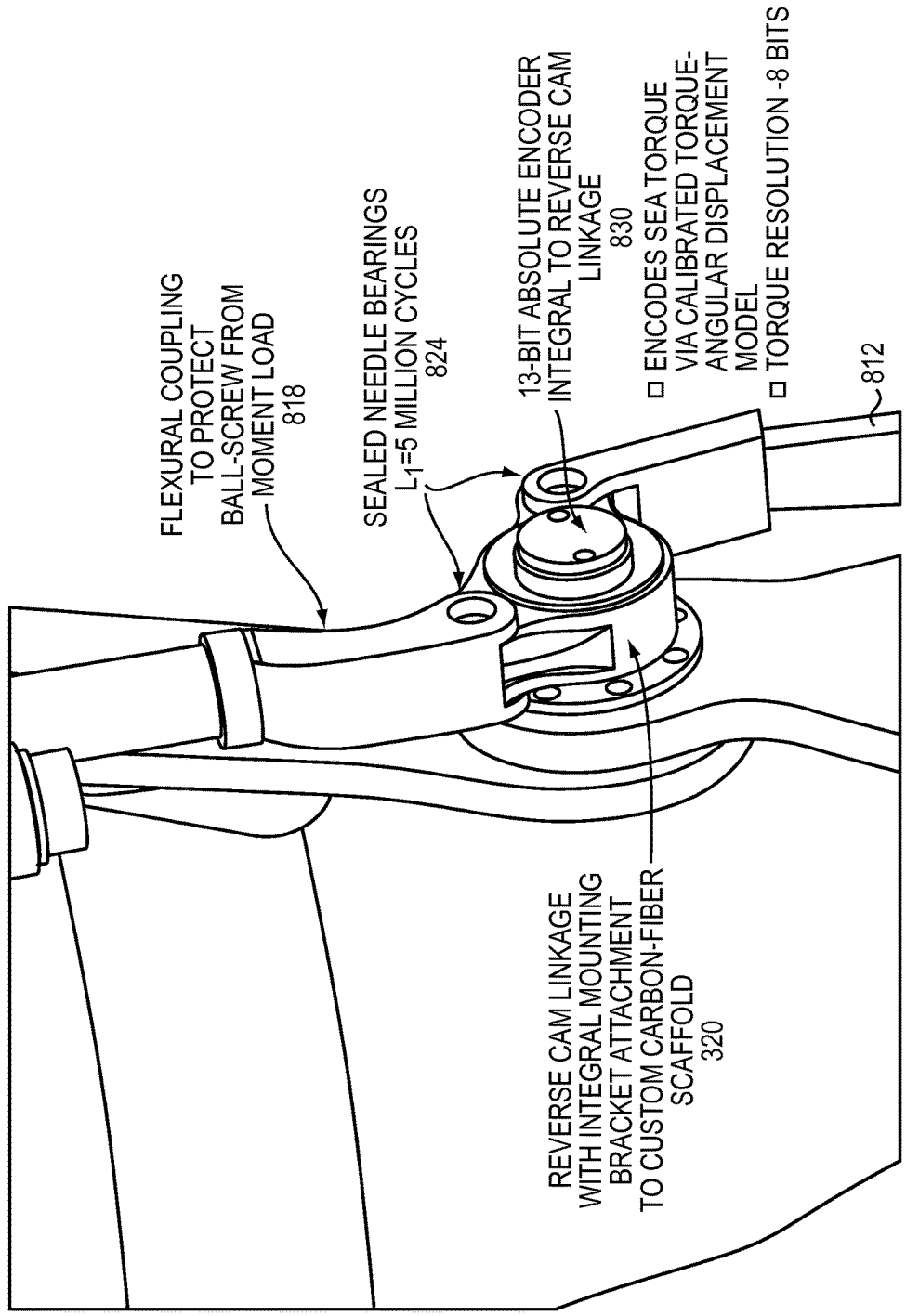

FIGS. 8a-8c depict a PKO device 800 that employs a buckled beam 812 as the series-elastic element of the SEA 802. The SEA 802 includes a high RPM brushless, permanent magnet motor 814 having an integral heat sink and an insulator. The motor 814 can be a radial motor, a transverse-flux motor, a stepping motor, etc. The SEA 802 also includes a sealed ball-screw mechanism 816 having a 14 mm diameter and 3 mm lead, in this embodiment. It should be understood that these dimensions are illustrative only and are not limiting.

The motor 814 is coupled to the buckled beam via a flexural coupling 818 to protect the ball-screw mechanism 816 from moment load, a reverse-cam linkage 820, and sealed needle bearings 824. The needle bearings 824 typically have L1 design life of over five million cycles (i.e., a design whereby 99% of a population survive longer than the reported design life with 95% statistical confidence). The PKO 800 also includes an integral pivot scaffold SEA support 826, coupled to the motor 814, and a foot support 828 (e.g., a custom nylon foot support), coupled to the buckled beam 812. The reverse-cam linkage 820 includes an encoder 830 that may be used to determine the SEA torque based on a torque-angular displacement model. The encoder 830 can be a 13-bit absolute encoder having a torque resolution of about 8 bits.

Figure 8D:
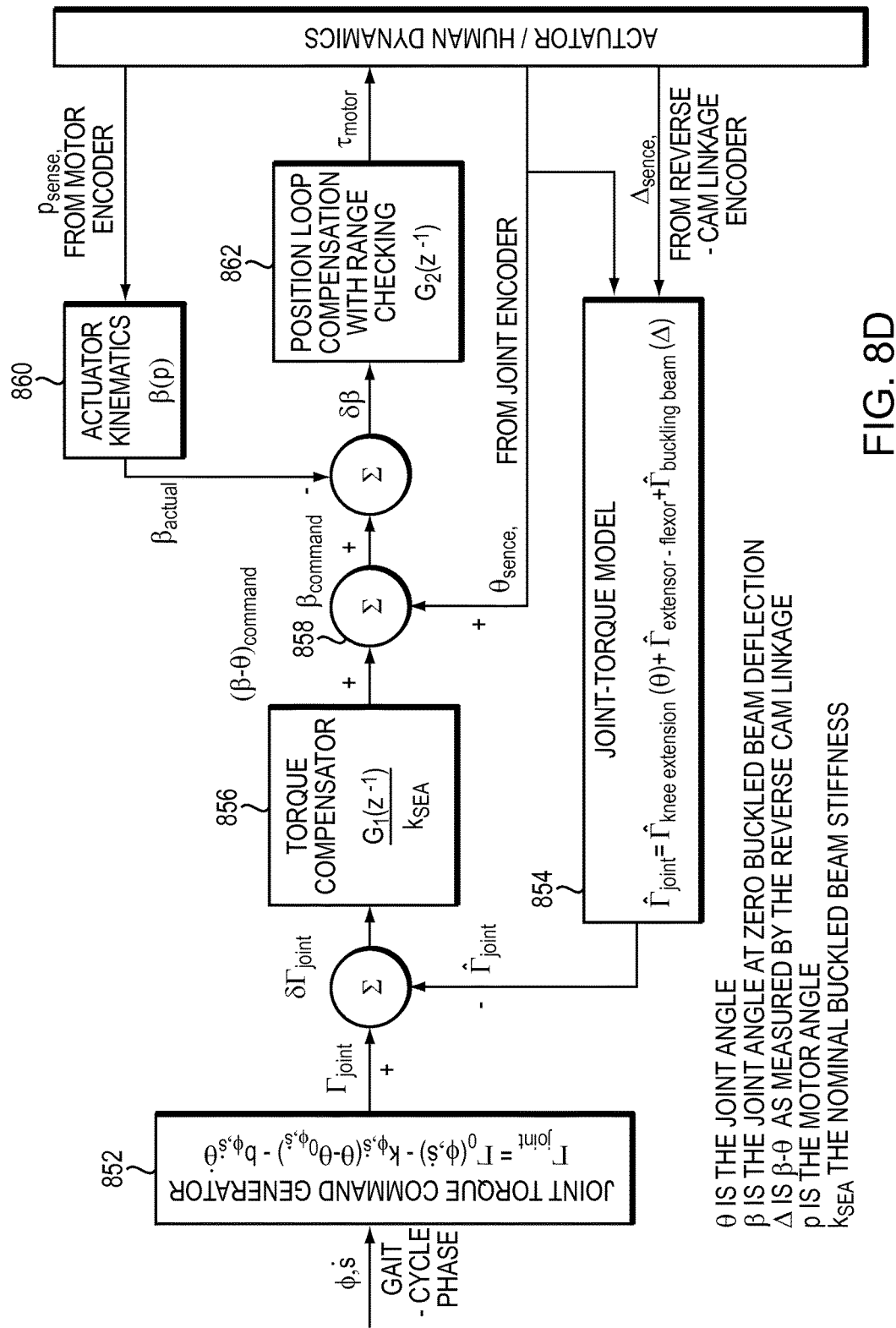
FIGS. 8d and 8e illustrate closed-loop control of the powered augmentation device depicted in FIGS. 8a-8c, according to two embodiments, respectively.

In one embodiment, the motor 814 is controlled in a closed loop. FIG. 8d illustrates one embodiment of an implementation of the closed-loop torque control in the PKO 800, in which the Joint Torque Command Generator 852 computes the commanded joint torque, $\Gamma_{joint}$, from terrain, $\varphi$, walking speed, $\dot{s}$, and gait-cycle phase as these are supplied from a State Controller (e.g., State and Actuator Controller 508, described with reference to FIG. 5). The Joint-Torque Model 854 estimates the actual applied joint torque, $\Gamma_{joint}$, from wearer knee extension, wearer extensor-flexor and buckling-beam 812 (for series-elasticity) torque contributions. The wearer contributions may be assumed to be a percentage of a normative amount or a percentage of the command torque. The contribution of the buckling-beam 812 (series elastic component of the SEA 802, in general) may be estimated from off-wearer calibration during testing of the PKO device 800.

The difference in the commanded and applied torque, $\delta\Gamma_{joint}$, is scaled by the nominal stiffness of the buckling beam 812 (generally, the SEA) and is passed through a proportional-integral-derivative (PID) compensator 856, $G_1$ ($z^{-1}$), to compute a commanded value of deflection, $\beta-\theta$, where $\theta$ is the joint angle and $\beta$ is the joint angle specified by the actuator for approximately zero buckled beam (SEA) deflection. $G_1$ is designed with at least integral compensation with saturation error limits to force substantially zero steady-state torque error and may typically include proportional and derivative terms. The sensed joint angle, $\theta_{sense}$, is added by an adder 858 to the deflection command to compute a commanded actuator angle, $\beta_{commanded}$.

The estimated actuator displacement is derived by actuator kinematics 860 by sensing the motor angle, p, which is used in a computational model, $\beta(p)$, of the actuator kinematics 860. The actuator error is supplied to a second PID compensator 862 with actuator range of motion limits to deliver a motor torque, $\tau_{motor}$, to drive the actuator 802. A brushless, permanent magnet motor, either radial, transverse flux, or stepping motor, is commutated electronically using a multiphase motor driver that delivers a torque-producing current component, $i_q$, to achieve the desired motor torque via the relation $\tau_{motor} = k_t i_q$, where $k_t$ is the motor torque constant in Nm/A. If a stepping motor is used, the motor can be stepped in a closed-loop fashion to align with the position command.

Figure 8E:
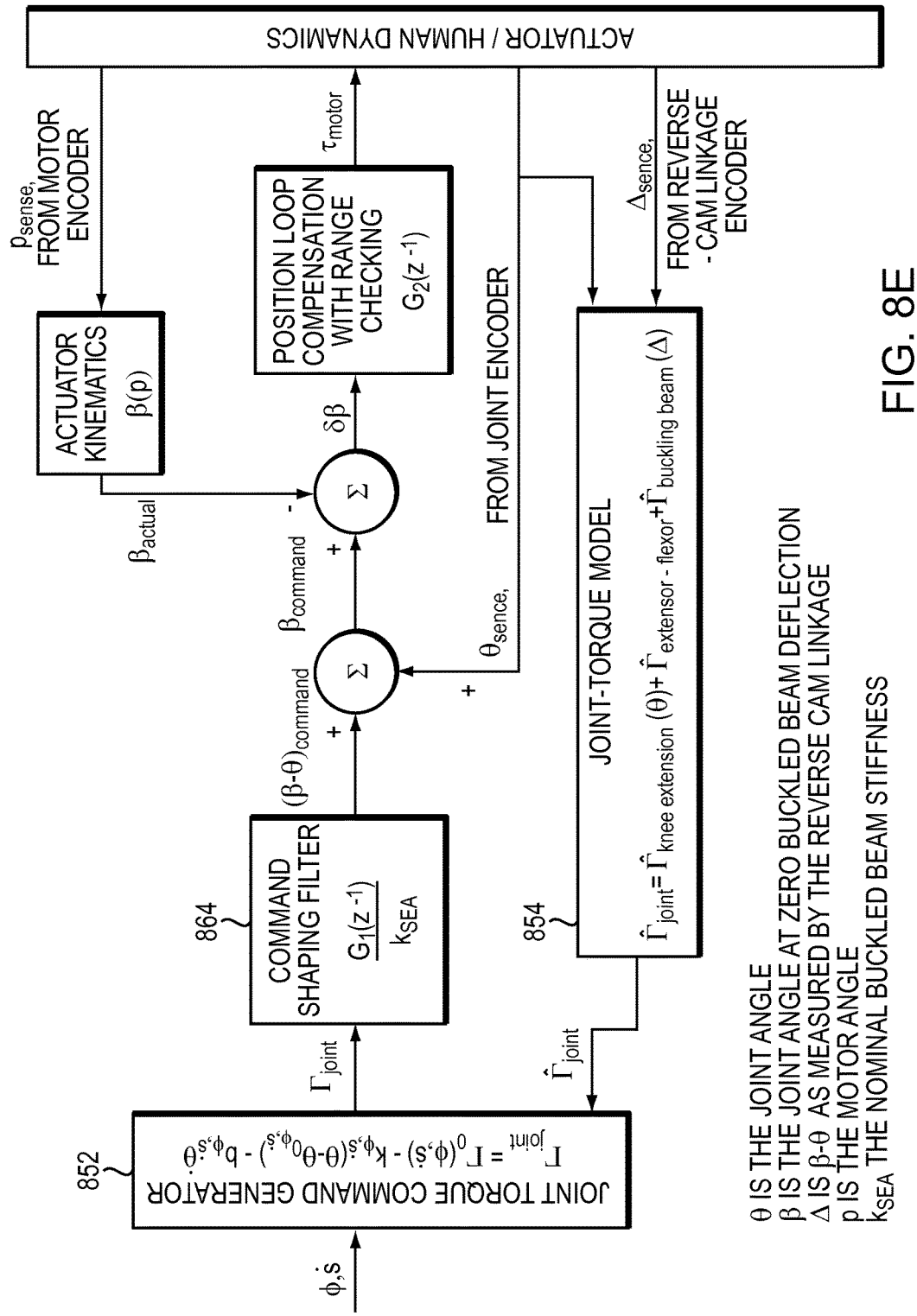

In another embodiment illustrated with reference to FIG. 8e, the Joint Torque Model 854 supplies and estimated joint torque to the Joint Torque Command generator 852, which determines the augmentation torque command, $\Gamma_{joint}$. The torque command is passed through a command shaping filter 864, having a transfer function $G_1(z^{-1})$ and a torque de-scaling, $$\frac{1}{k_{SEA}},$$

to create a high-fidelity deflection signal. The command shaping filter 864 may be a low-pass filter to ensure that the inner deflection control loop has sufficient response bandwidth to follow the command. Other embodiments may be implemented by those skilled in the art to deliver a joint torque response that closely matches the desired biomechanical response as this is achieved through modulation of impedance, joint equilibrium, and torque in accordance with gait-cycle phase, terrain and walking speed.

Figure 9:
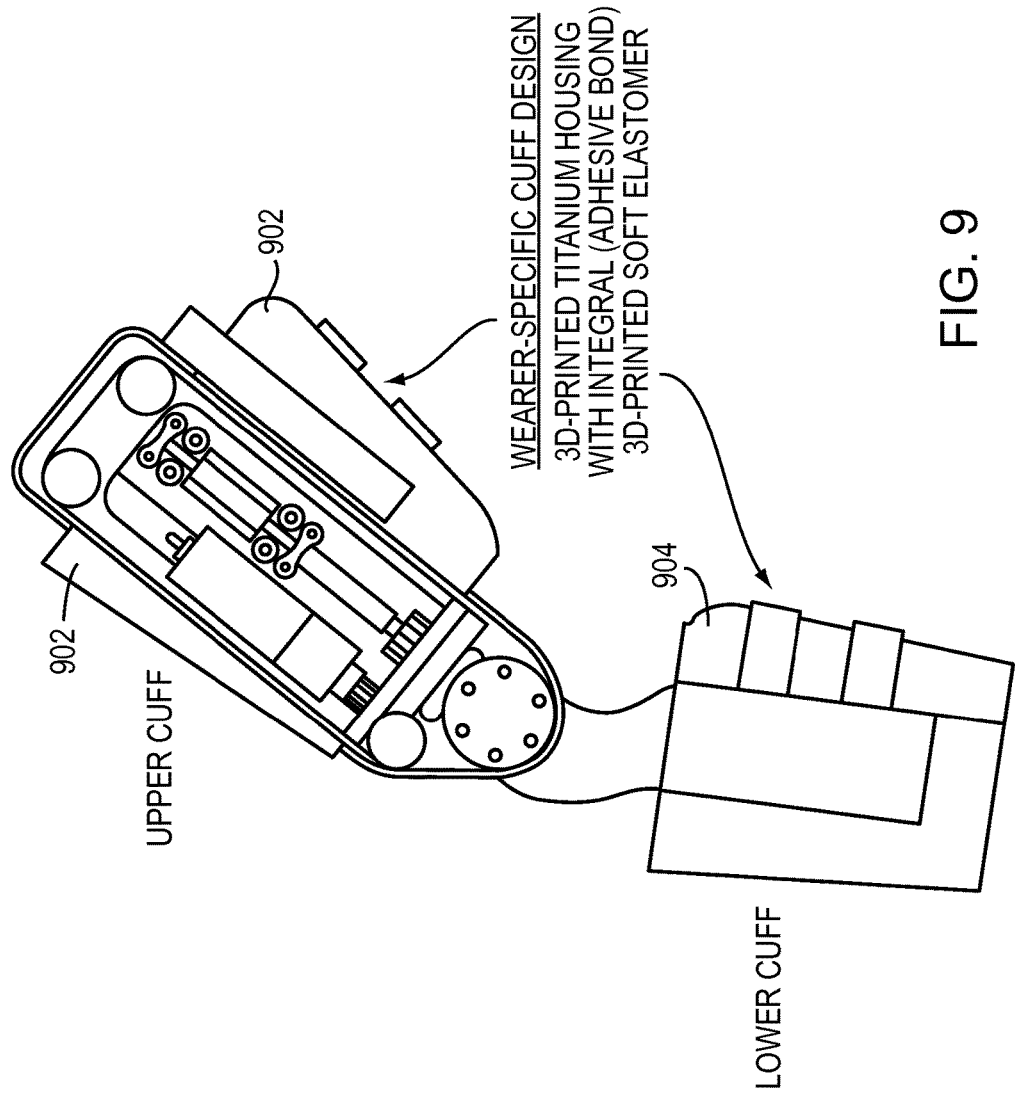
FIG. 9 illustrates seamless integration of a powered augmentation device with a leg of a human, according to one embodiment.

Seamless integration of the PKO platform 500 onto a wearer is desirable to ensure that the torque supplied by the PKO platform 500 is coupled efficiently to the joint (knee, ankle, etc.). With reference to FIG. 9, in some embodiments, a process is provided for custom manufacturing an upper cuff assembly 902 and a lower cuff assembly 904 to conform/couple directly to the wearer. For each wearer a three-dimensional scanning tool is employed to measure those body surfaces that must integrate with the PKO platform 500. From these surface measurements, lightweight titanium forms can be printed (e.g., using a direct-write process). These can be functionalized through heat treating to create the scaffold upon which a custom 3-D printed elastomer, with spatially-varying durometer, can be bonded to achieve the desired custom integration.

In some embodiments, the State and Actuator Controller 508 is adapted to kinematically reconstruct a joint path. Such reconstruction can be used to determine the terrain (e.g., whether the terrain is level ground, sloping ground, or stairs), and activity (i.e., whether the wearer is walking on level ground, upslope, or downslope, or walking up or down the stairs). The modulation of the toque, impedance, and joint equilibrium may be based on the terrain and activity as determined via the kinematic reconstruction.

Figure 10:
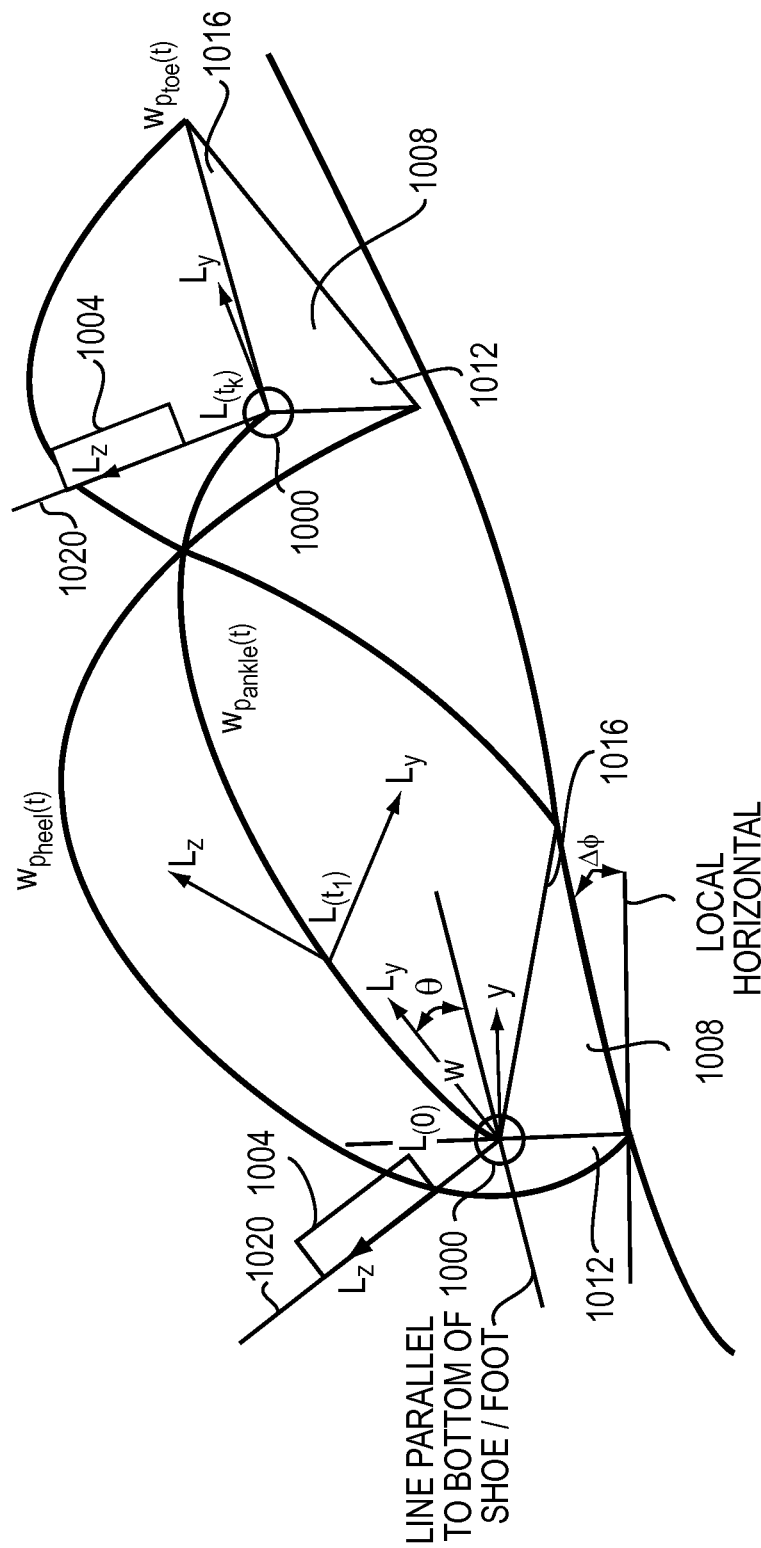
FIG. 10 depicts kinematic reconstruction by a controller for controlling a powered augmentation device according to one embodiment.

FIG. 10 illustrates a method for determining, via kinematic reconstruction, ankle joint 1000, heel 1012 and toe 1016 paths while using any PKO device (e.g., the PKO platforms 500, 800) based on the inertial pose of a lower leg member 1020 coupled to the ankle joint 1000, and the angle between the lower leg member 1020 and foot member 1008. Pose is the position and orientation of a coordinate system. The IMU (e.g., the IMU 510) may be coupled to the lower leg member 1020. The IMU may include a three-axis rate gyro for measuring angular rate and a three-axis accelerometer for measuring acceleration. Placing the inertial measurement unit on the lower leg member 1020 collocates the measurement of angular rate and acceleration for all three axes of the lower leg member 1020. The inertial measurement unit provides a six-degree-of-freedom estimate of the lower leg member 1020 pose, inertial (world frame referenced) orientation and ankle-joint 1000 (center of rotation of the ankle-foot) location.

In some embodiments, the lower leg member 1020 pose is used to compute the instantaneous location of the knee joint. By using knowledge of the ankle joint 1000 angle ($\theta$) the instantaneous pose of the bottom of the foot 1008 can be computed, including location of the heel 1012 and toe 1016. This information in turn can be used when the foot member 1008 is flat to measure the terrain angle in the plane defined by the rotational axis of the ankle joint/foot member. Mounting the inertial measurement unit on the lower leg member 1020 has advantages over other potential locations. Unlike if it were mounted on the foot member 1008, the lower leg member 1020 mounting protects against physical abuse and keeps it away from water exposure. Further, it eliminates the cable tether that would otherwise be needed if it were on the foot member 1008—thereby ensuring mechanical and electrical integrity. Finally, the lower leg member 1020 is centrally located within the kinematic chain of a hybrid system facilitating the computation of the thigh and torso pose with a minimum of additional sensors.

The inertial measurement unit can be used to calculate the orientation, $_{ankle}{}^{w}O$, position, $_{ankle}{}^{w}p$, and velocity, $_{ankle}{}^{w}v$, of the PKO platform in a ground-referenced world frame. $_{ankle}{}^{w}O$ may be represented by a quaternion or by a 3×3 matrix of unit vectors that define the orientation of the x, y and z axes of the ankle joint in relation to the world frame. The ankle joint 1000 coordinate frame is defined to be positioned at the center of the ankle joint axis of rotation with its orientation tied to the lower leg member 1020. From this central point, the position, velocity and acceleration can be computed. For points of interest in, for example, the foot (e.g., the heel 1012 or toe 1016), a foot member-to-ankle joint orientation transformation, $_{foot}{}^{ankle}O(\theta)$ is used to derive the position using the following relation:

$$_{point\text{-}of\text{-}interest}{}^{w}p = {}_{ankle}{}^{w}p + {}_{ankle}{}^{w}O(\gamma)_{foot}{}^{ankle}O(\theta)(^{foot}r_{point\text{-}of\text{-}interest})$$

where $$_{foot}^{ankle}O(\gamma) = \begin{bmatrix} 1 & 0 & 0 \\ 0 & \cos(\gamma) & -\sin(\gamma) \\ 0 & \sin(\gamma) & \cos(\gamma) \end{bmatrix}$$

where $\gamma$ is the inertial lower leg member angle, and $$_{foot}^{ankle}O(\theta) = \begin{bmatrix} 1 & 0 & 0 \\ 0 & \cos(\theta) & -\sin(\theta) \\ 0 & \sin(\theta) & \cos(\theta) \end{bmatrix}$$

where $\theta$ is the ankle joint angle.

In this embodiment, the inertial measurement unit, including the three-axis accelerometer and three-axis rate gyro, is located on the forward face at the top of the lower leg member 1020. It is advantageous to remove the effect of scale, drift and cross-coupling on the world-frame orientation, velocity and position estimates introduced by numerical integrations of the accelerometer and rate gyro signals Inertial navigation systems typically employ a zero-velocity update (ZVUP) periodically by averaging over an extended period of time, usually seconds to minutes. This placement of the inertial measurement unit is almost never stationary in the lower-extremity devices such as a PKO. However, the bottom of the foot is the only stationary location, and then only during the controlled dorsiflexion state of the gait cycle. An exemplary zero-velocity update method, which is not impacted by this limitation, for use with various embodiments of the invention is described further below.

To solve this problem, orientation, velocity and position integration of ankle joint is performed. After digitizing the inertial measurement unit acceleration, $IMU_a$, the ankle joint acceleration ($IMU_{a_{ankle}}$) is derived with the following rigid body dynamic equation:

$$IMU_{a_{ankle}} = IMU_a + IMU_{\vec{\omega}} \times IMU_{\vec{\omega}} \times X_{ankle}{}^{IMU}\vec{r} + \vec{\omega} X_{ankle}{}^{IMU}\vec{r}$$

where $IMU_{\vec{\omega}}$ and $IMU_{\vec{\dot{\omega}}}$ are the vectors of angular rate and angular acceleration, respectively, in the inertial measurement unit frame and X denotes the cross-product.

The relationship is solved $_{ankle}{}^w O = _{IMU}{}^w O$ similarly as in the equations above using standard strapdown inertial measurement unit integration methods, in accordance with the following relationships known to one skilled in the art:

$$^w_{ankle}\hat{\Phi} = {}^w\hat{\Omega}({}^w\hat{\omega})^w_{ankle}\hat{\Phi}$$

$$^w\hat{v}_{ankle} = {}^w\hat{a}_{ankle} - [0, 0, g]^T$$

$$^w\hat{p}_{ankle} = {}^w\hat{v}_{ankle}$$

$$^w_{foot}\hat{\Phi} = {}^w_{ankle}\hat{\Phi}^{ankle}_{foot}\hat{\Phi} = {}^w_{ankle}\hat{\Phi}\text{Rotation}_x(\hat{\Theta})$$

$$^w\hat{v}_{heel} = {}^w\hat{v}_{ankle} + {}^w\hat{\Omega}\left({}^w_{ankle}\hat{\Phi}\left[\hat{\Theta}\ 0\ 0\right]^T\right){}^w r_{heel-ankle}$$

$$^w\hat{v}_{toe} = {}^w\hat{v}_{ankle} + {}^w\hat{\Omega}\left({}^w_{ankle}\hat{\Phi}\left[\hat{\Theta}\ 0\ 0\right]^T\right){}^w r_{toe-ankle}$$

$$^w\hat{p}_{heel} = {}^w\hat{p}_{ankle} + {}^w r_{heel-ankle}$$

$$^w\hat{p}_{toe} = {}^w\hat{p}_{ankle} + {}^w r_{toe-ankle}$$

$$^w r_{heel-ankle} = {}^w_{foot}\hat{\Phi}^{foot}(r_{heel} - r_{ankle})$$

$$^w r_{toe-ankle} = {}^w_{foot}\hat{\Phi}^{foot}(r_{toe} - r_{ankle})$$

In the equations above, the matrix, $\hat{\Phi}$, will be used interchangeably with the orientation matrix, $_{IMU}{}^w O$. The world frame-referenced ankle joint velocity and position are then derived at a point in time after the time of the previous zero-velocity update (i-th zero-velocity update) based on the following:

$$^w v_{ankle}(t) = \int_{ZVUP(i)}^t ({}_{IMU}{}^w O)^{IMU} a_{ankle} dt$$

$$^w p_{ankle}(t) = \int_{ZVUP(i)}^t {}^w v_{ankle} dt$$

where $^w p_{ankle}(t=ZVUP(i))$ is reset to zero for all i.

Figure 11A:
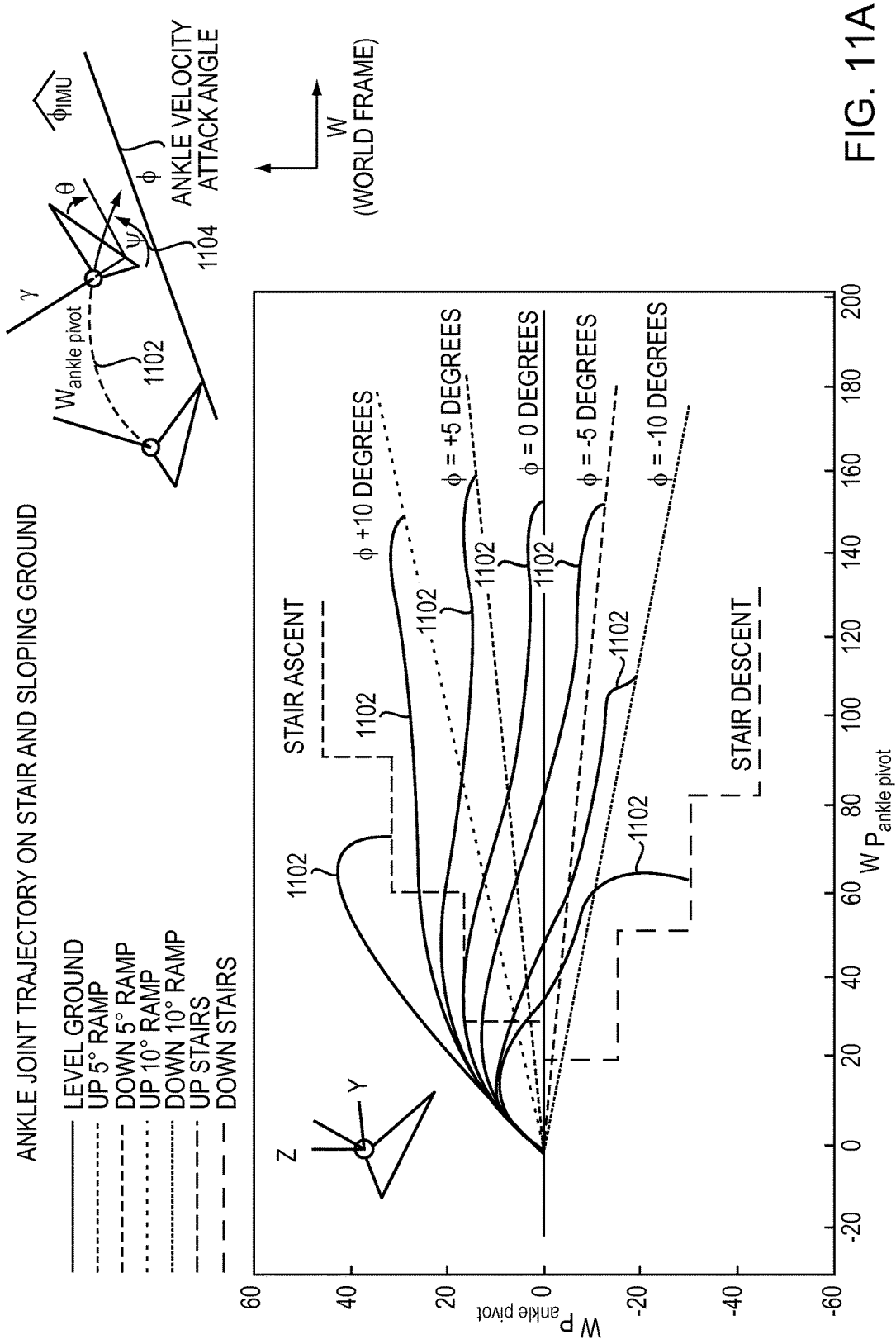
FIGS. 11a and 11b depict ankle and knee paths, respectively, each derived using measurements from an inertial measurement unit, according to one embodiment.

The six-degree-of-freedom inertial measurement unit (IMU) 510 of the PKO platform 500 or the IMU of the PKO device 800 is capable of computing the path of the ankle joint and the distal-end of the femur (knee) from which the IMU can discriminate and discern terrain modality—including stairs and slopes. With reference to FIG. 11*a*, inertially referenced ankle joint paths $^W p_{ankle\ joint}(t)$, and ankle-velocity-attack-angle 1104, $^W V_{ankle\ joint}$, on stairs and sloping ground can be used to discriminate stair ascent/descent from ascent/descent on sloping ground. The slope, $\phi$, can be estimated as $\hat{\phi}$ in swing using the relation:

$$\hat{\phi} = \tan^{-1}({}^W p_{ankle\ joint_z}(t), {}^W p_{ankle\ joint_y})$$

Figure 11B:
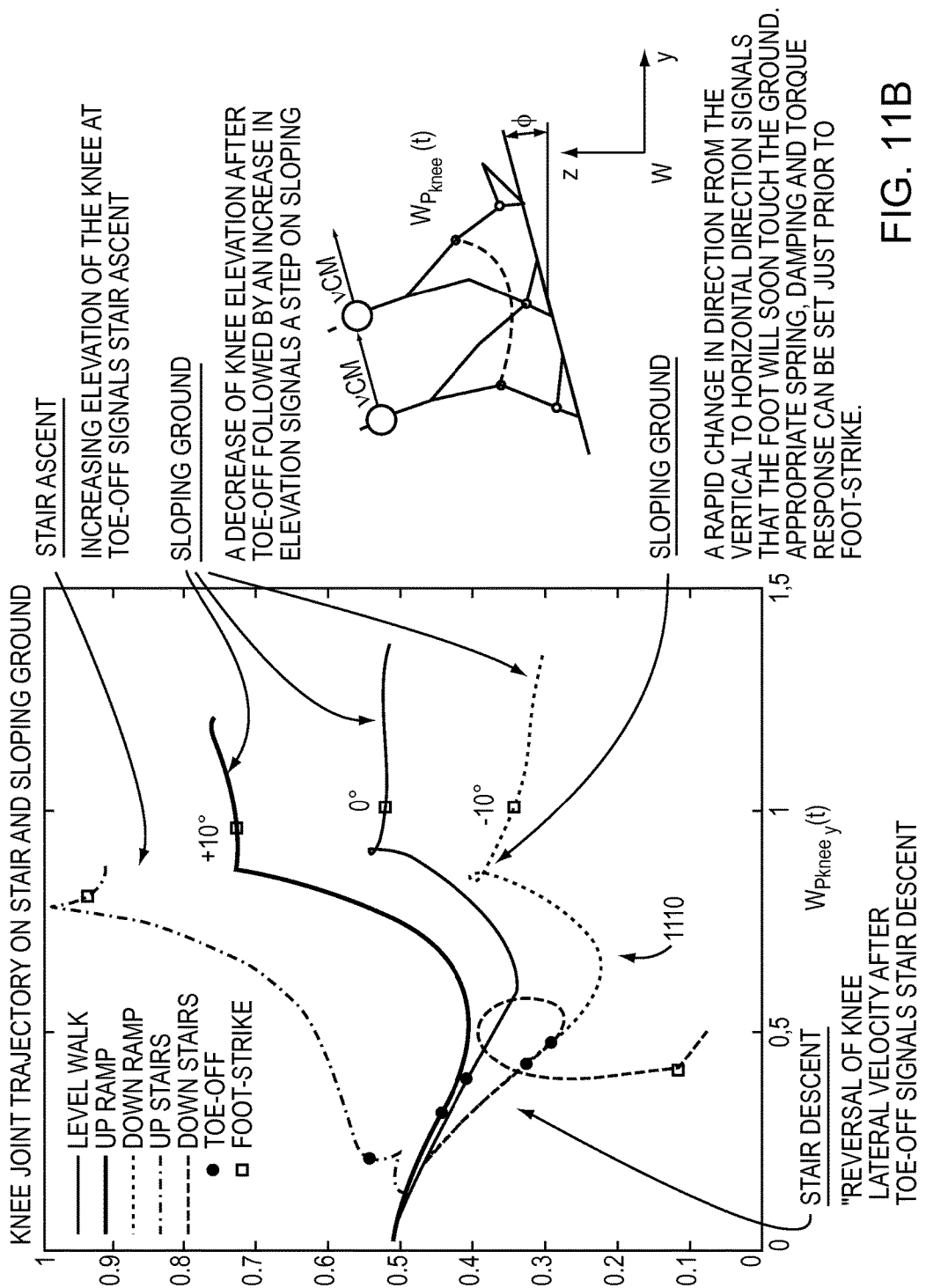

With reference to FIG. 11*b*, inertially-referenced knee path shape can be used to detect stair ascent/descent shortly after toe-off—enabling knee impedance and torque response to be configured prior to foot-strike on the stair. The "kink" 1110 in the knee path may signal impending foot strike on sloping ground, enabling a prediction of terrain slope using the ankle joint slope prediction described above with reference to FIG. 11*a*. Using the joint slope, speed and ankle velocity angle-of-attack, the joint equilibrium and impedance can be adjusted in preparation for the foot strike.

While the invention has been particularly shown and described with reference to specific embodiments, it will be understood by those skilled in the art that various changes in form and detail may be made therein without departing from the spirit and scope of the invention as defined by the appended claims. The scope of the invention is thus indicated by the appended claims and all changes that come within the meaning and range of equivalency of the claims are therefore intended to be embraced.

What is claimed is:

1. A powered human augmentation device for assisting a person walking on a surface, the device comprising:
    a powered actuator to supply to a joint at least one of an augmentation torque and an impedance comprising a linear spring component and a damping component;
    an inertial measurement unit (IMU) to generate a kinematic signal, the kinematic signal to include indications of positions of the joint during a gait cycle; and
    a controller to:
        determine whether a phase of the gait cycle is early- or mid-stance;
        receive the kinematic signal;
        reconstruct a path of the joint within the gait cycle based on the kinematic signal;
        estimate within the gait cycle a slope of a surface based on the reconstructed path;
        determine whether the estimated slope is substantially zero or negative; and
        modulate at least one of the augmentation torque and the impedance based on the phase of the gait cycle and the estimated slope of the surface to provide at least a biomimetic response, wherein the modulating comprises at least one of:
            sending a control signal to the powered actuator based on a determination that the phase of the gait cycle is one of early stance or mid stance and a determination that the estimated slope of the surface is substantially zero, the control signal to cause the powered actuator to provide the modulated impedance such that contribution of the linear spring component of the modulated impedance is greater than contribution of the damping component of the modulated impedance, or
            sending a control signal to the powered actuator based on a determination that the phase of the gait cycle is one of early stance or mid stance and a determination that the estimated slope of the surface is negative, the control signal to cause the power actuator to provide the modulated impedance such that contribution of the damping component is substantially greater compared to the contribution of the damping component based on a determination that the estimated slope of the surface is substantially zero.

2. The powered human augmentation device of claim 1, wherein the estimated slope is indicative of a walking mode such that level-ground walking mode corresponds to a substantially zero slope, downslope walking mode corresponds to a negative slope, and upslope walking mode corresponds to a positive slope.

3. The powered human augmentation device of claim 2, wherein the downslope walking mode comprises descending stairs and the upslope walking mode comprises ascending stairs.

4. The powered human augmentation device of claim 1, wherein the joint is a knee.

5. The powered human augmentation device of claim 1, wherein the controller is adapted to estimate walking speed, and at least one of the augmentation torque and the impedance is based on the estimated walking speed.

6. The powered human augmentation device of claim 1, wherein the augmentation torque comprises a non-conservative propulsive torque, the controller to:
determine whether the phase of the gait cycle is one of early stance or mid stance;
determine whether the estimated slope of the surface is positive; and
send a control signal to the powered actuator based on a determination that the phase of the gait cycle is one of early stance or mid stance and a determination that the estimated slope of the surface is positive, the control signal to cause the powered actuator to provide-the nonconservative propulsive torque such that the modulated augmentation torque is greater than the modulated augmentation torque applied based on a determination that the estimated slope of the surface is substantially zero.

7. The powered human augmentation device of claim 1, the controller to:
determine whether the phase of the gait cycle is late stance; and
send a control signal to the powered actuator based on a determination that the phase of the gate cycle is late stance, the control signal to cause the powered actuator to provide the modulated augmentation torque such that the modulated augmentation torque corresponds to a reflex torque that is related to the estimated slope of the surface.

8. The powered human augmentation device of claim 1, wherein the controller is adapted to model, during a swing phase of the gait cycle, a joint equilibrium as a second-order response to a joint-position goal to be achieved prior to a next phase of the gait cycle.

9. The powered human augmentation device of claim 8 further comprising a joint angle sensor to provide a joint angle signal to the controller, wherein if the controller determines, based on the joint angle signal, that the joint is substantially fully flexed, the powered actuator is adapted to adjust both the augmentation torque and the impedance to be substantially zero, during a swing phase of the gait cycle.

10. The powered human augmentation device of claim 8, wherein if the controller determines the phase of the gait cycle to be early swing, the augmentation torque is modulated according to the modeled joint-equilibrium such that a joint equilibrium corresponds to the joint-position goal.

11. The powered human augmentation device of claim 8, wherein if the controller determines the phase of the gait cycle to be early swing, the impedance is modulated according to the modeled joint-equilibrium such that a joint equilibrium corresponds to the joint-position goal.

12. The powered human augmentation device of claim 1, wherein the IMU comprises at least one of an accelerometer and a gyroscope.

13. The powered human augmentation device of claim 1, wherein the IMU comprises a first set of sensors associated with the joint and a second set of sensors associated with another joint, and the controller is adapted to:
kinematically reconstruct a path of the other joint within the gait cycle based on signals from the second set of sensors; and
associate the path of the other joint with the path of the joint to estimate the slope.

14. The powered human augmentation device of claim 1, wherein the augmentation torque is modulated according to a positive-force feedback.

15. The powered human augmentation device of claim 14, wherein the augmentation torque modulated according to the positive-force feedback, in combination with a natural joint torque supplied by the human, approximates at least a normal joint torque.

16. The powered human augmentation device of claim 14, wherein the positive-force feedback comprises a gain and an exponent.

17. The powered human augmentation device of claim 16, wherein modulating comprises adjusting at least one of the gain and the exponent according to at least one of the estimated slope and walking speed.

18. The powered human augmentation device of claim 1, wherein the controller is adapted to modulate the augmentation torque according to a scaling factor.

19. The powered human augmentation device of claim 1 further comprising a communication interface for receiving a protocol, and the controller is adapted to attenuate the augmentation torque according to the received protocol.

20. The powered human augmentation device of claim 1, wherein the augmentation torque is supplied in addition to natural joint torque supplied by the person to achieve at least a pre-determined total joint torque response.

21. The powered human augmentation device of claim 1, wherein the controller is adapted to apply a closed-loop torque control at the joint.

22. The powered human augmentation device of claim 21, wherein the controller is adapted to:
model the toque at the joint; and
determine the phase of the gait cycle based on the modeled joint torque.

23. The powered human augmentation device of claim 1, wherein the powered actuator comprises a series-elastic actuator.

24. The powered human augmentation device of claim 23, wherein the series-elastic actuator comprises a transverse-flux motor.

25. The powered human augmentation device of claim 23, wherein the series-elastic actuator comprises a bilateral spring and a cable drive.

26. The powered human augmentation device of claim 23, wherein the series-elastic actuator comprises a unidirectional spring.

27. The powered human augmentation device of claim 23, wherein the series-elastic actuator comprises a buckled beam.

28. A powered human augmentation device for assisting a person walking on a surface, the device comprising:
a powered actuator to supply to a joint at least one of an augmentation torque and an impedance comprising a linear spring component and a damping component;
an inertial measurement unit (IMU) to generate a kinematic signal, the kinematic signal to include indications of positions of the joint during a gait cycle; and
a controller to:

determine whether a phase of the gait cycle is early- or mid-stance;
receive the kinematic signal;
reconstruct a path of the joint within the gait cycle based on the kinematic signal;
estimate within the gait cycle a slope of a surface based on the reconstructed path;
determine whether the estimated slope is substantially zero or negative; and
modulate at least one of the augmentation torque and the impedance based on the phase of the gait cycle and the estimated slope of the surface to provide at least a biomimetic response, wherein the modulating comprises sending a control signal to the powered actuator based on a determination that the phase of the gait cycle is one of early stance or mid stance and a determination that the estimated slope of the surface is substantially zero, the control signal to cause the powered actuator to provide the modulated impedance such that contribution of the linear spring component of the modulated impedance is greater than contribution of the damping component of the modulated impedance.

29. A powered human augmentation device for assisting a person walking on a surface, the device comprising:
a powered actuator to supply to a joint at least one of an augmentation torque and an impedance comprising a linear spring component and a damping component;
an inertial measurement unit (IMU) to generate a kinematic signal, the kinematic signal to include indications of positions of the joint during a gait cycle; and
a controller to:
determine whether a phase of the gait cycle is early- or mid-stance;
receive the kinematic signal;
reconstruct a path of the joint within the gait cycle based on the kinematic signal;
estimate within the gait cycle a slope of a surface based on the reconstructed path;
determine whether the estimated slope is substantially zero or negative; and
modulate at least one of the augmentation torque and the impedance based on the phase of the gait cycle and the estimated slope of the surface to provide at least a biomimetic response, wherein the modulating comprises sending a control signal to the powered actuator based on a determination that the phase of the gait cycle is one of early stance or mid stance and a determination that the estimated slope of the surface is negative, the control signal to cause the power actuator to provide the modulated impedance such that contribution of the damping component is substantially greater compared to the contribution of the damping component based on a determination that the estimated slope of the surface is substantially zero.

* * * * *